US008750986B2

(12) United States Patent
Zhu et al.

(10) Patent No.: US 8,750,986 B2
(45) Date of Patent: Jun. 10, 2014

(54) SYSTEM AND METHOD FOR ESTIMATING CLUSTERING OF ELECTRODES IN NEUROSTIMULATION SYSTEM

(75) Inventors: Changfang Zhu, Valencia, CA (US); David K. L. Peterson, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 298 days.

(21) Appl. No.: 13/184,411

(22) Filed: Jul. 15, 2011

(65) Prior Publication Data

US 2012/0016445 A1    Jan. 19, 2012

Related U.S. Application Data

(60) Provisional application No. 61/365,280, filed on Jul. 16, 2010.

(51) Int. Cl.
*A61N 1/08* (2006.01)

(52) U.S. Cl.
USPC ............................................................ 607/2

(58) Field of Classification Search
USPC ........................................................ 607/59
See application file for complete search history.

(56) References Cited

U.S. PATENT DOCUMENTS

| | | | |
|---|---|---|---|
| 5,083,571 A * | 1/1992 | Prichep | 600/544 |
| 6,516,227 B1 | 2/2003 | Meadows et al. | |
| 6,895,280 B2 | 5/2005 | Meadows et al. | |
| 6,993,384 B2 | 1/2006 | Bradley et al. | |
| 7,146,219 B2 | 12/2006 | Sieracki et al. | |
| 7,317,948 B1 | 1/2008 | King et al. | |
| 7,650,184 B2 | 1/2010 | Walter | |
| 8,019,439 B2 | 9/2011 | Kuzma et al. | |
| 8,380,301 B2 | 2/2013 | Zhu | |
| 2004/0176804 A1 | 9/2004 | Palti | |
| 2006/0206163 A1 | 9/2006 | Wahlstrand et al. | |
| 2007/0168004 A1 | 7/2007 | Walter | |
| 2007/0168007 A1 | 7/2007 | Kuzma et al. | |
| 2008/0125833 A1 | 5/2008 | Bradley et al. | |
| 2010/0137944 A1 | 6/2010 | Zhu | |
| 2011/0054551 A1 | 3/2011 | Zhu et al. | |
| 2012/0016447 A1 | 1/2012 | Zhu et al. | |

OTHER PUBLICATIONS

Timm, Neil. Applied Multivariate Analysis. Springer-Verlag, New York. 2002:515-555.*
File History of U.S. Appl. No. 13/184,454, filed Jul. 15, 2011, inventor: Changfang Zhu.
Office Action dated Apr. 29, 2013 in U.S. Appl. No. 13/184,454, filed Jul. 15, 2011, inventor: Changfang Zhu et al., (21pages).

(Continued)

*Primary Examiner* — Luther Behringer
(74) *Attorney, Agent, or Firm* — Vista IP Law Group LLP

(57) ABSTRACT

A method and neurostimulation control system for programming electrodes disposed adjacent tissue of a patient. The electrodes are initially assigned to a plurality of electrode subsets to be evaluated. A pair of immediately neighboring ones of the electrode subsets is determined, and merged into a new electrode subset that includes all electrodes in the pair of immediately neighboring electrode subsets. The new electrode subset is included within the plurality of electrode subsets to be evaluated, while the pair of immediately neighboring electrode subsets is excluded from the plurality of electrode sets to be evaluated. These steps are repeated until all the electrode subsets have been merged into a single electrode subset. A clustering relationship of the electrodes is identified, and the electrodes are programmed based on the identified clustering relationship of the electrodes.

26 Claims, 19 Drawing Sheets

(56) References Cited

OTHER PUBLICATIONS

File History of U.S. Appl. No. 61/030,506, Temporary Neurostimulation Lead Identification Device, Inventor: John Michael Barker, et al., filed Feb. 21, 2008.

File History of U.S. Appl. No. 61/119,669, Method and Apparatus for Determining Relative Positioning Between Neurostimulation Leads, Inventor: Changfang Zhu, et al., filed Dec. 3, 2008.

* cited by examiner

SYSTEM AND METHOD FOR ESTIMATING CLUSTERING OF ELECTRODES IN NEUROSTIMULATION SYSTEM

RELATED APPLICATION DATA

The present application claims the benefit under 35 U.S.C. §119 to U.S. provisional patent application Ser. No. 61/365,280, filed Jul. 16, 2010. The foregoing application is hereby incorporated by reference into the present application in its entirety.

FIELD OF THE INVENTION

The present inventions relate to tissue stimulation systems, and more particularly, to neurostimulation systems for programming neurostimulation leads.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Also, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes one or more neurostimulation leads implanted at the desired stimulation site and an implantable neurostimulator, such as an implantable pulse generator (IPG), implanted remotely from the stimulation site, but coupled either directly to the leads or indirectly to the leads via one or more lead extensions in cases where the length of the leads is insufficient to reach the IPG. Thus, electrical pulses can be delivered from the neurostimulator to the leads to stimulate the tissue and provide the desired efficacious therapy to the patient.

In the context of an SCS procedure, one or more neurostimulation leads are introduced through the patient's back into the epidural space, such that the electrodes carried by the leads are arranged in a desired pattern and spacing to create an electrode array. One type of commercially available neurostimulation lead is a percutaneous lead, which comprises a cylindrical body with ring electrodes, and can be introduced into contact with the affected spinal tissue through a Touhy-like needle, which passes through the skin, between the desired vertebrae, and into the epidural space above the dura layer. For unilateral pain, a percutaneous lead is placed on the corresponding lateral side of the spinal cord. For bilateral pain, a percutaneous lead is placed down the midline of the spinal cord, or two or more percutaneous leads are placed down the respective sides of the midline of the spinal cord, and if a third lead is used, down the midline of the special cord. After proper placement of the neurostimulation leads at the target area of the spinal cord, the leads are anchored in place at an exit site to prevent movement of the leads. To facilitate the location of the neurostimulator away from the exit point of the leads, lead extensions are sometimes used.

Whether or not lead extensions are used, the proximal ends of the neurostimulation leads exiting the spinal column are passed through a tunnel subcutaneously formed along the torso of the patient to a subcutaneous pocket (typically made in the patient's abdominal or buttock area) where a neurostimulator is implanted. The subcutaneous tunnel can be formed using a tunneling tool over which a tunneling straw may be threaded. The tunneling tool can be removed, the leads threaded through the tunneling straw, and then the tunneling straw removed from the tunnel while maintaining the leads in place within the tunnel.

The neurostimulation leads are then connected directly to the neurostimulator by inserting the proximal ends of the stimulation leads within one or more connector ports of the IPG or connected to lead extensions, which are then inserted into the connector ports of the IPG. The IPG can then be operated to generate electrical pulses that are delivered, through the electrodes, to the targeted tissue, and in particular, the dorsal column and dorsal root fibers within the spinal cord.

The stimulation creates the sensation known as paresthesia, which can be characterized as an alternative sensation that replaces the pain signals sensed by the patient. Intra-operatively (i.e., during the surgical procedure), the neurostimulator may be operated to test the effect of stimulation and adjust the parameters of the stimulation (e.g., the electrodes that are acting as anodes or cathodes, as well as the amplitude, duration, and rate of the stimulation pulses). The patient may provide verbal feedback regarding the presence of paresthesia over the pain area, and based on this feedback, the lead positions may be adjusted and re-anchored if necessary. A computerized programming system, such as Bionic Navigator®, available from Boston Scientific Neuromodulation Corporation, can be used to facilitate selection of the stimulation parameters. Any incisions are then closed to fully implant the system. Post-operatively (i.e., after the surgical procedure has been completed), a clinician can adjust the stimulation parameters using the computerized programming system to re-optimize the therapy.

The efficacy of SCS is related to the ability to stimulate the spinal cord tissue corresponding to evoked paresthesia in the region of the body where the patient experiences pain. Thus, the working clinical paradigm is that achievement of an effective result from SCS depends on the neurostimulation lead or leads being placed in a location (both longitudinal and lateral) relative to the spinal tissue such that the electrical stimulation will induce paresthesia located in approximately the same place in the patient's body as the pain (i.e., the target of treatment). If a lead is not correctly positioned relative to the tissue or relative to another lead, it is possible that the patient will receive little or no benefit from an implanted SCS system. Thus, correct lead placement can mean the difference between effective and ineffective pain therapy.

Multi-lead configurations have been increasingly used in electrical stimulation applications (e.g., neurostimulation, cardiac resynchronization therapy, etc.). In the neurostimulation application of SCS, the use of multiple leads that are grouped together in close proximity to each other at one general region of the patient (e.g., side-by-side parallel leads along the spinal cord of the patient), increases the stimulation area and penetration depth (therefore coverage), as well as enables more combinations of anodic and cathodic electrodes for stimulation, such as transverse multipolar (bipolar, tripolar, or quadra-polar) stimulation, in addition to any longitudinal single lead configuration. In more advanced applications, multiple leads may be placed in different locations of the patient. For example, in an SCS application, one lead may be placed along the cervical region of the spinal cord, and another lead may be placed along the lumbar region of the spinal cord. As another example, in a combined SCS/PNS application, one lead may be placed along the spinal cord of the patient, and another lead may be placed in a peripheral location of a patient (e.g., an arm or a leg).

Whether the multiple leads are implanted in the patient in close proximity to each other at a particular location or implanted in the patient at separate locations, selection of cathodes/anodes requires the identification of the electrodes that are positioned close to each other and knowledge of the relative positions of the electrodes that are to be activated as the cathodes or anodes. Conventional electrical field-based techniques, such as those described in U.S. Pat. No. 6,993,384, entitled "Apparatus and Method for Determining the Relative Position and Orientation of Neurostimulation Leads," and U.S. patent application Ser. No. 12/623,976, entitled "Method and Apparatus for Determining Relative Positioning Between Neurostimulation Leads" (now U.S. Pat. No. 8,380,301), which are expressly incorporated herein by reference, have been developed to estimate the positions of the electrodes relative to each other by determining longitudinal offset and/or transverse separation between the leads. These techniques usually assume that the electrodes are arranged in-line along each lead and the arrangement of the electrode array is known so that certain patterns of the induced electrical field can be examined.

If not already taken into account by the programming system, information related to the arrangement of electrode arrays may be obtained through user input if it is available (e.g., a user can enter the spatial orientation of the leads and/or electrodes obtained from a recent radiographic image into the programming system). However, radiographic imaging may not always be available, and even when it is, the images do not allow for identification of each electrode in the array unless certain prior information is available, e.g., lead type, lead-port mapping and electrode configuration. If such prior information is limited, identifying the electrode arrays may be difficult. This problem may be more complicated when, for example, different types of extensions (e.g., splitters) are used to connect the leads to the neurostimulator, which may result in an electrode array configuration that is different from the physical electrode array arrangement. Furthermore, lead position determination software installed in current neurostimulation systems oftentimes need to be updated to accommodate new or unknown lead designs.

There, thus, remains a need for an improved generic technique for identifying electrodes that are in proximity to each other, the relative positioning between the electrodes, and the configuration of the electrodes.

SUMMARY OF THE INVENTION

In accordance with a first aspect of the present inventions, a neurostimulation control system for use with a plurality of electrodes is provided. The neurostimulation control system comprises a user interface configured for receiving an input from a user, and at least one processor configured for, in response to the user input, (a) initially assigning the electrodes to a plurality of electrode subsets to be evaluated, and (b) determining a pair of immediately neighboring ones of the electrode subsets.

In one embodiment, the processor(s) is configured for determining the pair of immediately neighboring electrode subsets by determining relative proximities between pairs of the electrode subsets, and selecting the pair of electrode subsets that has the minimum relative proximity therebetween as the determined pair of immediately neighboring electrode subsets. As one example, the processor(s) may be configured for selecting the pair of electrode subsets as the determined pair of immediately neighboring electrode subsets by determining one of the following: (1) the minimum electrode proximity between the respective pair of electrode subsets; (2) the maximum electrode proximity between the respective pair of electrode subsets; and (3) the average electrode proximity between the respective pair of electrode subsets. The electrode proximities may be determined based on the measurement of electrical parameters. For example, the neurostimulation control system may comprise monitoring circuitry configured for generating an electrical signal and measuring an electrical parameter (e.g., electrical field potential) between electrodes in response to the electrical signal, in which case, the processor(s) may be configured for determining the pair of immediately neighboring ones of the electrode subsets to be evaluated based on the measured electrical parameter.

The processor(s) is further configured for (c) merging the pair of immediately neighboring electrode subsets into a new electrode subset that includes all electrodes in the pair of immediately neighboring electrode subsets, (d) including the new electrode subset within the plurality of electrode subsets to be evaluated while excluding the pair of immediately neighboring electrode subsets from the plurality of electrode sets to be evaluated, and (e) repeating steps (b)-(d), e.g., until all the electrode subsets have been merged into a single electrode subset.

The processor(s) is further configured for (f) identifying a clustering relationship of the electrodes based at least in part on step (e).

In one embodiment, the processor(s) is configured for determining a pair of electrode subsets closest in proximity to each other than any other pair of electrode subsets in proximity to each other as the pair of immediately neighboring electrode subsets, and identifying the clustering relationship of the electrodes comprises by arranging the electrodes in hierarchical clustering structures.

In another embodiment, the processor(s) is configured for including the new electrode subset and a single electrode closest in proximity to the new electrode subset within the pair of immediately neighboring electrode subsets subsequently determined during step (b), and identifying the clustering relationship of the electrodes by arranging the single electrodes in an order in which they are included within the pair of immediately neighboring electrode subsets.

The neurostimulation control system further comprises a controller configured for programming the electrodes based on the identified clustering relationship of the electrodes. For example, the controller may select at least one of the electrodes as a cathode and select at least another of the electrodes as an anode based on the identified clustering relationship of the electrodes. As another example, the controller may select a plurality of groups of the electrodes to create a respective plurality of stimulation regions based on the identified clustering relationship of the electrodes. The processor(s) and controller may be contained within an external control device. Optionally, the neurostimulation control system comprises a display configured for displaying the identified clustering relationship of the electrodes.

In accordance with a second aspect of the present inventions, a method of programming electrodes disposed adjacent tissue of a patient is provided. The method comprises (a) initially assigning the electrodes to a plurality of electrode subsets to be evaluated, (b) determining a pair of immediately neighboring ones of the electrode subsets, (c) merging the pair of immediately neighboring electrode subsets into a new electrode subset that includes all electrodes in the pair of immediately neighboring electrode subsets, (d) including the new electrode subset within the plurality of electrode subsets to be evaluated while excluding the pair of immediately neighboring electrode subsets from the plurality of electrode sets to be evaluated, (e) repeating steps (b)-(d), (f) identifying a clustering relationship of the electrodes based at least in part on step (e), and (g) programming the electrodes based on the identified clustering relationship of the electrodes. These steps and any optional steps may be performed in the same manner at that in which the processor(s) and controller performed the steps described above.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a multi-lead system such as a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
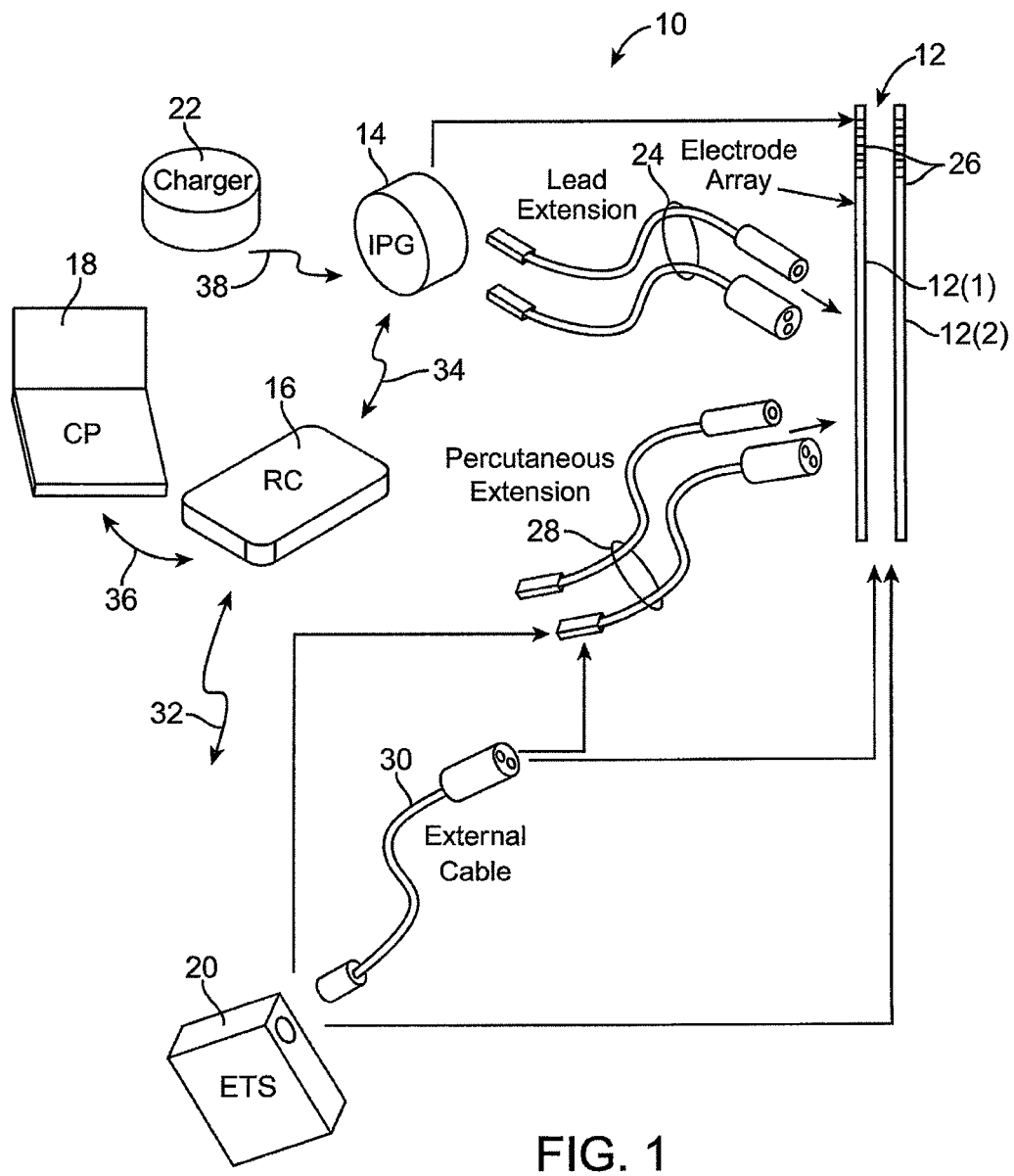
FIG. 1 is plan view of one embodiment of a spinal cord stimulation (SCS) system arranged in accordance with the present inventions.

Turning first to FIG. 1, an exemplary SCS system 10 generally comprises a plurality of percutaneous neurostimulation leads 12 (in this case, two percutaneous leads 12(1) and 12(2)), an implantable pulse generator (IPG) 14, an external remote control (RC) 16, a Clinician's Programmer (CP) 18, an External Trial Stimulator (ETS) 20, and an external charger 22.

The IPG 14 is physically connected via two lead extensions 24 to the neurostimulation leads 12, which carry a plurality of electrodes 26 arranged in an array. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters. The IPG 14 and stimulation leads 12 can be provided as an implantable neurostimulation kit, along with, e.g., a hollow needle, a stylet, a tunneling tool, and a tunneling straw. Further details discussing implantable kits are disclosed in U.S. Application Ser. No. 61/030,506, entitled "Temporary Neurostimulation Lead Identification Device," which is expressly incorporated herein by reference.

The ETS 20 may also be physically connected via percutaneous lead extensions 28 or external cable 30 to the neurostimulation lead 12. The ETS 20, which has similar pulse generation circuitry as the IPG 14, also delivers electrical stimulation energy in the form of a pulse electrical waveform to the electrode array 26 in accordance with a set of stimulation parameters. The major difference between the ETS 20 and the IPG 14 is that the ETS 20 is a non-implantable device that is used on a trial basis after the neurostimulation lead 12 has been implanted and prior to implantation of the IPG 14, to test the responsiveness of the stimulation that is to be provided. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation lead 12 is implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
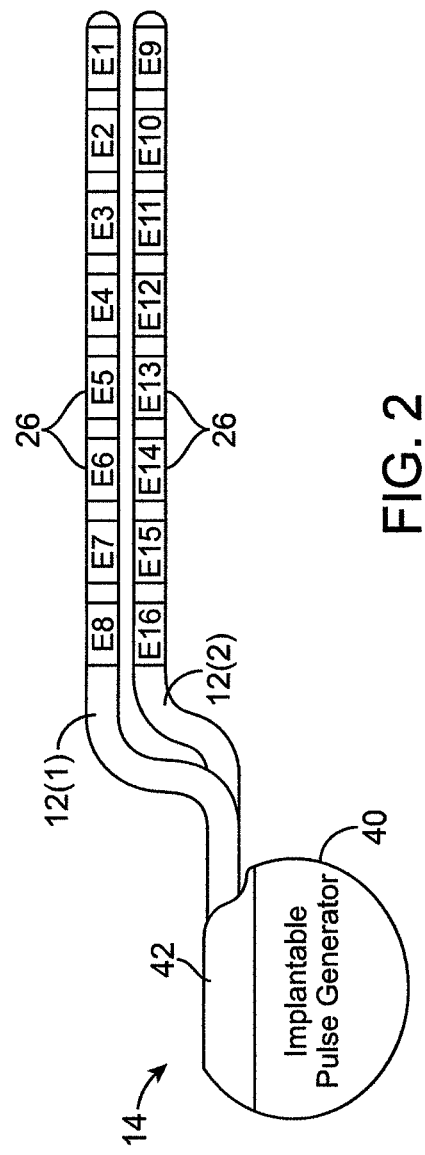
FIG. 2 is a plan view of an implantable pulse generator (IPG) and two neurostimulation leads used in the SCS system of FIG. 1.

Referring now to FIG. 2, the external features of the neurostimulation leads 12 and the IPG 14 will be briefly described. Each of the neurostimulation leads 12 has eight electrodes 26 (respectively labeled E1-E8 and E9-E16). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

The IPG 14 comprises an outer case 40 for housing the electronic and other components (described in further detail below). The outer case 40 is composed of an electrically conductive, biocompatible material, such as titanium, and forms a hermetically sealed compartment wherein the internal electronics are protected from the body tissue and fluids. In some cases, the outer case 40 may serve as an electrode. The IPG 14 further comprises a connector 42 to which the proximal ends of the neurostimulation leads 12 mate in a manner that electrically couples the electrodes 26 to the internal electronics (described in further detail below) within the outer case 40. To this end, the connector 42 includes two ports (not shown) for receiving the proximal ends of the three percutaneous leads 12. In the case where the lead extensions 24 are used, the ports may instead receive the proximal ends of such lead extensions 24.

As will be described in further detail below, the IPG 14 includes pulse generation circuitry that provides electrical stimulation energy to the electrodes 26 in accordance with a set of parameters. Such parameters may comprise electrode combinations, which define the electrodes that are activated as anodes (positive), cathodes (negative), and turned off (zero), and electrical pulse parameters, which define the pulse amplitude (measured in milliamps or volts depending on whether the IPG 14 supplies constant current or constant voltage to the electrodes), pulse duration (measured in microseconds), pulse rate (measured in pulses per second), and pulse shape.

With respect to the pulse patterns provided during operation of the SCS system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case 40, so that the electrical current has a path from the energy source contained within the IPG case 40 to the tissue and a sink path from the tissue to the energy source contained within the case. Electrical energy may be transmitted to the tissue in a monopolar or multipolar (e.g., bipolar, tripolar, etc.) fashion.

Monopolar delivery occurs when a selected one or more of the lead electrodes 26 is activated along with the case 40 of the IPG 14, so that electrical energy is transmitted between the selected electrode 26 and case 40. Monopolar delivery may also occur when one or more of the lead electrodes 26 are activated along with a large group of lead electrodes located remotely from the one or more lead electrodes 26 so as to create a monopolar effect; that is, electrical energy is conveyed from the one or more lead electrodes 26 in a relatively isotropic manner. Bipolar delivery occurs when two of the lead electrodes 26 are activated as anode and cathode, so that electrical energy is transmitted between the selected electrodes 26. Tripolar delivery occurs when three of the lead electrodes 26 are activated, two as anodes and the remaining one as a cathode, or two as cathodes and the remaining one as an anode.

Figure 3:
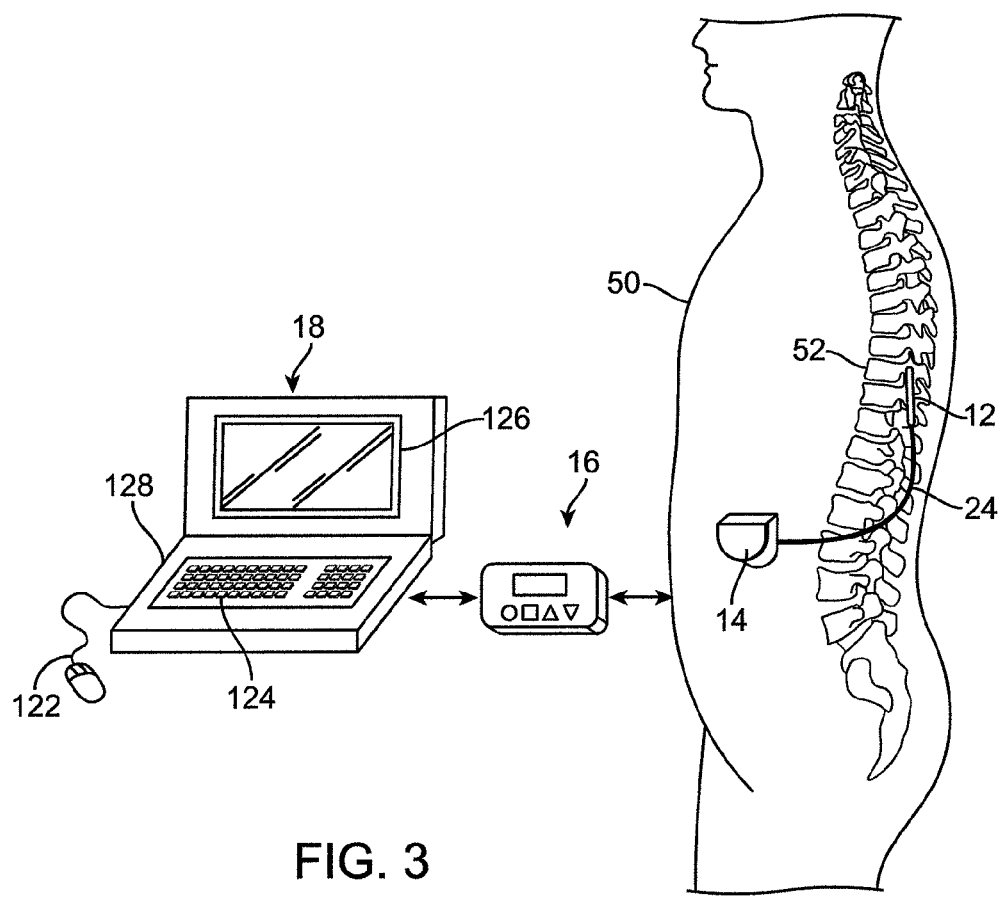
FIG. 3 is a plan view of the SCS system of FIG. 1 in use with a patient.

Referring to FIG. 3, the neurostimulation leads 12 are implanted within the spinal column 46 of a patient 48. The preferred placement of the neurostimulation leads 12 is adjacent, i.e., resting near, or upon the dura, adjacent to the spinal cord area to be stimulated. Due to the lack of space near the location where the neurostimulation leads 12 exit the spinal column 46, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the neurostimulation leads 12. As there shown, the CP 18 communicates with the IPG 14 via the RC 16. While the neurostimulation leads 12 are illustrated as being implanted near the spinal cord area of a patient, the neurostimulation leads 12 may be implanted anywhere in the patient's body, including a peripheral region, such as a limb, or the brain. After implantation, the IPG 14 is used to provide the therapeutic stimulation under control of the patient.

Figure 4:
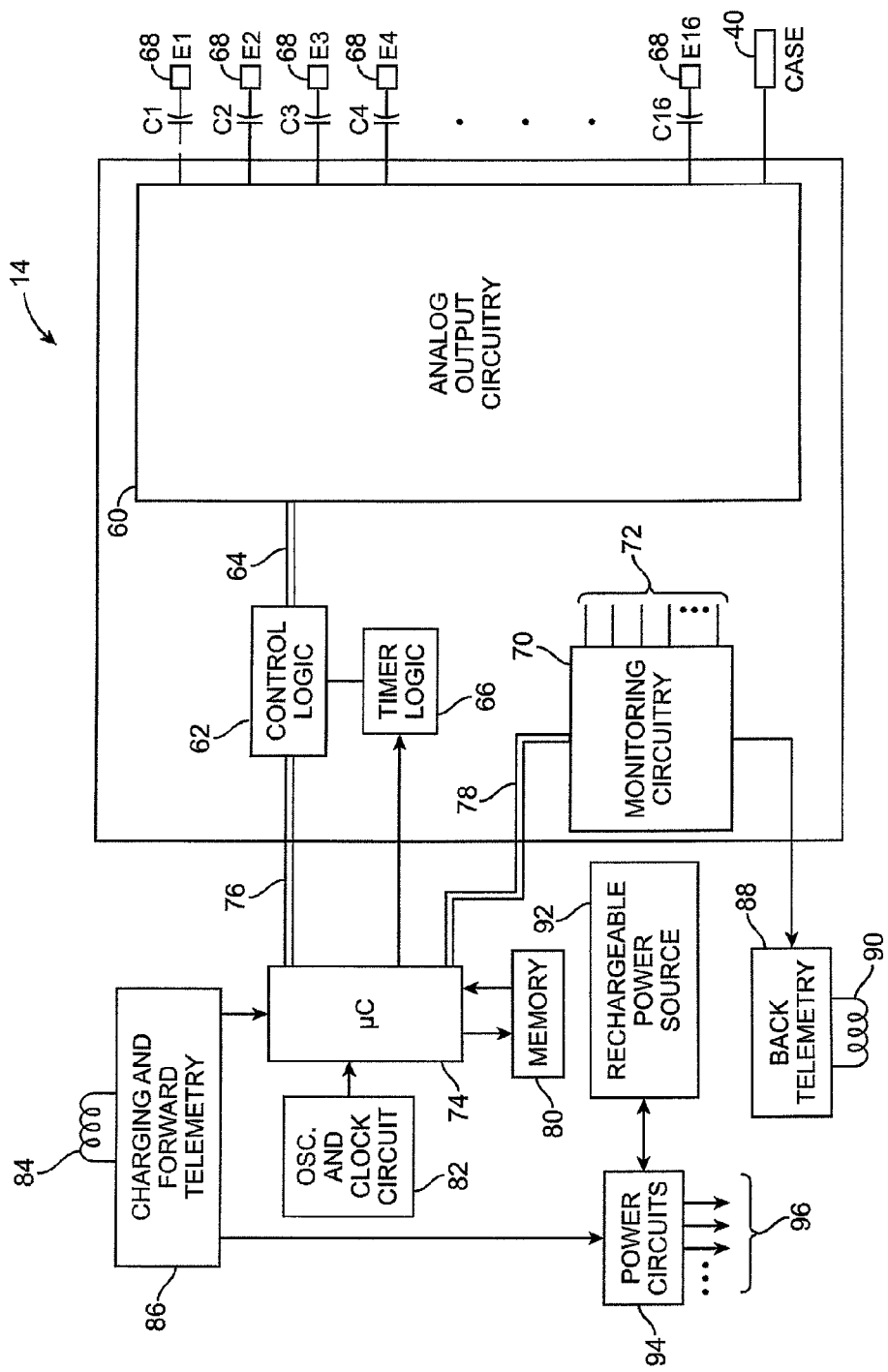
FIG. 4 is a block diagram of the internal components of the IPG of FIG. 1.

Turning next to FIG. 4, the main internal components of the IPG 14 will now be described. The IPG 14 includes stimulation output circuitry 60 configured for generating electrical stimulation energy in accordance with a defined pulsed waveform having a specified pulse amplitude, pulse rate, pulse width, pulse shape, and burst rate under control of control logic 62 over data bus 64. Control of the pulse rate and pulse width of the electrical waveform is facilitated by timer logic circuitry 66, which may have a suitable resolution, e.g., 10 μs. The stimulation energy generated by the stimulation output circuitry 60 is output via capacitors C1-C16 to electrical terminals 68 corresponding to the electrodes 26.

The analog output circuitry 60 may either comprise independently controlled current sources for providing stimulation pulses of a specified and known amperage to or from the electrical terminals 68, or independently controlled voltage sources for providing stimulation pulses of a specified and known voltage at the electrical terminals 68 or to multiplexed current or voltage sources that are then connected to the electrical terminals 68. The operation of this analog output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 further comprises monitoring circuitry 70 for monitoring the status of various nodes or other points 72 throughout the IPG 14, e.g., power supply voltages, temperature, battery voltage, and the like. Notably, the electrodes 26 fit snugly within the epidural space of the spinal column, and because the tissue is conductive, electrical measurements can be taken from the electrodes 26. Significantly, the monitoring circuitry 70 is configured for taking such electrical measurements, so that, as will be described in further detail below, the relative proximities between pairs of electrodes may be determined.

Electrical signals can be transmitted between electrodes carried by one of the neurostimulation lead 12 and one or more other electrodes (e.g., electrodes on the same neurostimulation lead 12, electrodes on the other neurostimulation lead 12, the case 40 of the IPG 12, or an electrode affixed to the tissue), and then electrical parameters can be measured in response to the transmission of the electrical signals. In the illustrated embodiment, the electrical measurements taken by the monitoring circuitry 70 for the purpose of determining the relative proximity between electrode pairs are electrical field potentials, although other suitable measurements, such as, e.g., an electrical impedance or an evoked potential measurement, can be obtained.

Distances between electrodes can be determined based on the measured electrical parameters in a conventional manner, such as, e.g., any one or more of the manners disclosed in U.S. Pat. No. 6,993,384, entitled "Apparatus and Method for Determining the Relative Position and Orientation of Neurostimulation Leads," U.S. patent application Ser. No. 12/550,136, entitled "Method and Apparatus for Determining Relative Positioning Between Neurostimulation Leads," and U.S. patent application Ser. No. 12/623,976, entitled "Method and Apparatus for Determining Relative Positioning Between Neurostimulation Leads" (now U.S. Pat. No. 8,380,301), which are expressly incorporated herein by reference.

The electrical parameter measurements can be made on a sampled basis during a portion of the time while the electrical stimulus pulse is being applied to the tissue, or immediately subsequent to stimulation, as described in U.S. patent application Ser. No. 10/364,436, which has previously been incorporated herein by reference. Alternatively, the electrical data measurements can be made independently of the electrical stimulation pulses, such as described in U.S. Pat. Nos. 6,516,227 and 6,993,384, which are expressly incorporated herein by reference.

The IPG 14 further comprises processing circuitry in the form of a microcontroller 74 that controls the control logic 62 over data bus 76, and obtains status data from the monitoring circuitry 70 via data bus 78. The microcontroller 74 additionally controls the timer logic 66. The IPG 14 further comprises memory 80 and an oscillator and clock circuit 82 coupled to the microcontroller 74. The microcontroller 74, in combination with the memory 80 and oscillator and clock circuit 82, thus comprise a microprocessor system that carries out a program function in accordance with a suitable program stored in the memory 80. Alternatively, for some applications, the function provided by the microprocessor system may be carried out by a suitable state machine.

Thus, the microcontroller 74 generates the necessary control and status signals, which allow the microcontroller 74 to control the operation of the IPG 14 in accordance with a selected operating program and parameters. In controlling the operation of the IPG 14, the microcontroller 74 is able to individually generate electrical pulses at the electrodes 26 using the analog output circuitry 60, in combination with the control logic 62 and timer logic 66, thereby allowing each electrode 26 to be paired or grouped with other electrodes 26, including the monopolar case electrode, and to control the polarity, amplitude, rate, and pulse width through which the current stimulus pulses are provided.

The IPG 14 further comprises an alternating current (AC) receiving coil 84 for receiving programming data (e.g., the operating program and/or stimulation parameters) from the RC 16 in an appropriate modulated carrier signal, and charging and forward telemetry circuitry 86 for demodulating the carrier signal it receives through the AC receiving coil 84 to recover the programming data, which programming data is then stored within the memory 80, or within other memory elements (not shown) distributed throughout the IPG 14.

The IPG 14 further comprises back telemetry circuitry 88 and an alternating current (AC) transmission coil 90 for sending informational data (including the field potential and impedance data) sensed through the monitoring circuitry 70 to the RC 16. The back telemetry features of the IPG 14 also allow its status to be checked. For example, any changes made to the stimulation parameters are confirmed through back telemetry, thereby assuring that such changes have been correctly received and implemented within the IPG 14. Moreover, upon interrogation by the RC 16, all programmable settings stored within the IPG 14 may be uploaded to the RC 16.

The IPG 14 further comprises a rechargeable power source 92 and power circuits 94 for providing the operating power to the IPG 14. The rechargeable power source 92 may, e.g., comprise a lithium-ion or lithium-ion polymer battery. The rechargeable battery 92 provides an unregulated voltage to the power circuits 94. The power circuits 94, in turn, generate the various voltages 96, some of which are regulated and some of which are not, as needed by the various circuits located within the IPG 14. The rechargeable power source 92 is recharged using rectified AC power (or DC power converted from AC power through other means, e.g., efficient AC-to-DC converter circuits) received by the AC receiving coil 84. To recharge the power source 92, an external charger (not shown), which generates the AC magnetic field, is placed against, or otherwise adjacent, to the patient's skin over the implanted IPG 14. The AC magnetic field emitted by the external charger induces AC currents in the AC receiving coil 84. The charging and forward telemetry circuitry 86 rectifies the AC current to produce DC current, which is used to charge the power source 92. While the AC receiving coil 84 is described as being used for both wirelessly receiving communications (e.g., programming and control data) and charging energy from the external device, it should be appreciated that the AC receiving coil 84 can be arranged as a dedicated charging coil, while another coil, such as coil 90, can be used for bi-directional telemetry.

It should be noted that the diagram of FIG. 4 is functional only, and is not intended to be limiting. Those of skill in the art, given the descriptions presented herein, should be able to readily fashion numerous types of IPG circuits, or equivalent circuits, that carry out the functions indicated and described. It should be noted that rather than an IPG for the neurostimulator, the SCS system 10 may alternatively utilize an implantable receiver-stimulator (not shown) connected to the neurostimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 5:
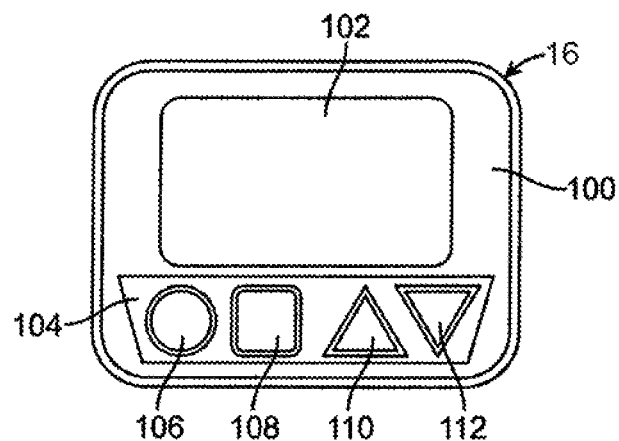
FIG. 5 is a plan view of a remote control that can be used in the SCS system of FIG. 1.

Referring now to FIG. 5, one exemplary embodiment of an RC 16 will now be described. As previously discussed, the RC 16 is capable of communicating with the IPG 14, CP 18, or ETS 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touchscreen capabilities. The button pad 104 includes a multitude of buttons 106, 108, 110, and 112, which allow the IPG 14 to be turned ON and OFF, provide for the adjustment or setting of stimulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 106 to switch between screen displays and/or parameters. The buttons 110 and 112 serve as up/down buttons that can be actuated to increase or decrease any of stimulation parameters of the pulse generated by the IPG 14, including pulse amplitude, pulse width, and pulse rate.

Figure 6:
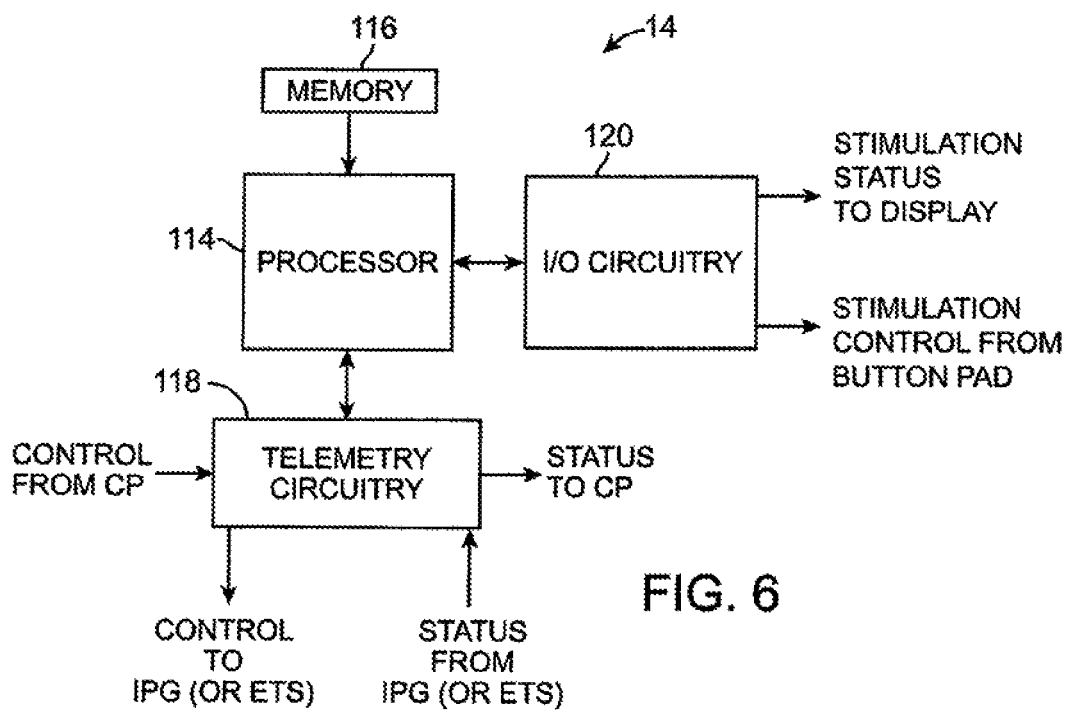
FIG. 6 is a block diagram of the internal componentry of the remote control of FIG. 5.

Referring to FIG. 6, the internal components of an exemplary RC 16 will now be described. The RC 16 generally includes a processor 114 (e.g., a microcontroller), memory 116 that stores an operating program for execution by the processor 114, and telemetry circuitry 118 for transmitting control data (including stimulation parameters and requests to provide status information) to the IPG 14 (or ETS 20) and receiving status information (including the measured electrical data) from the IPG 14 (or ETS 20) via link 34 (or link 32) (shown in FIG. 1), as well as receiving the control data from the CP 18 and transmitting the status data to the CP 18 via link 36 (shown in FIG. 1). The RC 16 further includes input/output circuitry 120 for receiving stimulation control signals from the button pad 104 and transmitting status information to the display screen 102 (shown in FIG. 5). Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the physician or clinician to readily determine the desired stimulation parameters to be programmed into the IPG 14, as well as the RC 16. Thus, modification of the stimulation parameters in the programmable memory of the IPG 14 after implantation is performed by a clinician using the CP 18, which can directly communicate with the IPG 14 or indirectly communicate with the IPG 14 via the RC 16. That is, the CP 18 can be used by the physician or clinician to modify operating parameters of the electrode array 26 near the spinal cord.

As shown in FIG. 3, the overall appearance of the CP 18 is that of a laptop personal computer (PC), and in fact, may be implemented using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 (or ETS 20) to allow the optimum stimulation parameters to be determined based on patient feedback and for subsequently programming the IPG 14 (or ETS 20) with the optimum stimulation parameters.

Figure 7:
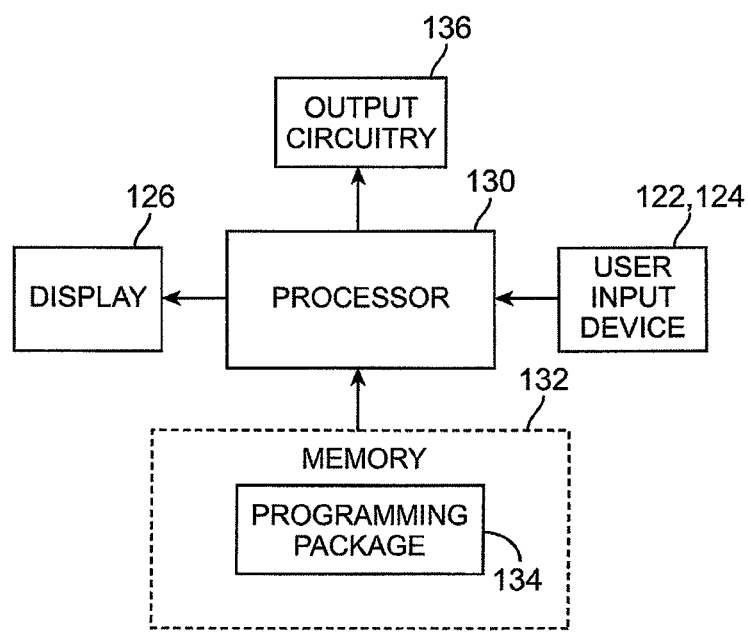
FIG. 7 is a block diagram of the components of a clinician's programmer that can be used in the SCS system of FIG. 1.

To allow the clinician to perform these functions, the CP 18 includes a mouse 122, a keyboard 124, and a programming display screen 126 housed in a case 128. It is to be understood that in addition to, or in lieu of, the mouse 122, other directional programming devices may be used, such as a joystick, or directional keys included as part of the keys assigned to the keyboard 124. As shown in FIG. 7, the CP 18 generally includes a processor 130 (e.g., a central processor unit (CPU)) and memory 132 that stores a stimulation programming package 134, which can be executed by the processor 130 to allow a clinician to program the IPG 14 (or ETS 20) and RC 16. The CP 18 further includes output circuitry (e.q., telemetry circuitry) 136 for downloading stimulation parameters to the RC 16 and uploading stimulation parameters already stored in the memory 116 of the RC 16 via link 36 (shown in FIG. 1). The telemetry circuitry 136 is also configured for transmitting the control data (including stimulation parameters and requests to provide status information) to the IPG 14 (or ETS 20) and receiving status information (including the measured electrical data) from the IPG 14 (or ETS 20) indirectly via the RC 16.

Significantly, the CP 18 is configured for identifying a clustering relationship between the electrodes 26, such that the electrodes 26 can be more efficiently programmed without having prior knowledge of the type of lead or electrode array arrangement. For example, knowing this clustering relationship provides information related to which combination of electrodes should be programmed with the same polarity (e.g., one cluster of neighboring electrodes can be efficiently programmed as cathodes, and another cluster of neighboring electrodes can be efficiently programmed as anodes) and/or information related to the electrode combinations that correlate to different anatomical regions of the patient (e.g., one large cluster of neighboring electrodes may be correlated to the cervical spinal region of a patient, and another large cluster of neighboring electrodes may be correlated to the lumbar spinal region of the patient), such that the electrodes can be programmed to create multiple foci of stimulation respectively over the multiple anatomical regions. As will be appreciated from the following discussion, the electrode clustering techniques described herein provide an effective search path (for any lead configuration) to find a successively larger combination of a set of closely positioned electrode for programming.

For example, if the neurostimulation leads 12 are arranged in a parallel relationship with a staggered ¾ electrode offset, with the second neurostimulation lead 12(2) positioned below the first neurostimulation lead 12(1), as shown in the fluoroscopic image of one clinical case illustrated in FIG. 8a, the CP 18 may identify a cluster of three electrodes (e.g., electrodes E1, E2, and E9) and another cluster of two electrodes (e.g., electrodes E4 and E11). Knowing this, the cluster of three electrodes may, e.g., be programmed as cathodes, and the cluster of two electrodes may, e.g., be programmed as anodes. Or, the CP 18 may identify a cluster of four electrodes (e.g., electrodes E7, E8, E14, and E15) and another cluster of four electrodes (e.g., electrodes E4, E5, E11, and E12). Knowing this, the cluster of four electrodes may, e.g., be programmed as cathodes, and the other cluster of four electrodes may, e.g., be programmed as anodes. Or, the CP 18 may successively add or subtract electrodes to an electrode group over several electrode testing iterations (e.g., adding electrode E3 to the group of electrodes consisting of electrodes E9 and E10, testing the new electrode group of electrodes E3, E9, and E10; adding electrode E2 to the group of electrodes consisting of electrodes E3, E9, and E10, testing the new electrode group of electrodes E2, E3, E9, and E10, etc.)

As another example, if the neurostimulation leads 12 are arranged in a rostro-caudal manner, with the first neurostimulation lead 12(1) below the second neurostimulation lead 12(2), as shown in the fluoroscopic image of another clinical case illustrated in FIG. 8b, the CP 18 may identify a cluster of eight electrodes (e.g., electrodes E1-E8) and another cluster of electrodes (e.g., electrodes E9-E16). Knowing this, the cluster of eight electrodes may, e.g., be programmed to create one stimulation region, and the other cluster of eight electrodes may be programmed to create another stimulation region.

In identifying the clustering relationship between the electrodes 26, the CP 18 performs a nearest neighbor analysis of the electrodes 26. The problem of nearest neighbor analysis can be characterized as given a set of points M in the data space S, and a query point (or a set of query points) p in the same space S, find a point in the set of points M that is closest to the query point p. The analogue problem with respect to an electrode array can be characterized as for any designated electrode (or a set of electrodes), find the one (or a set) in the remaining electrode sets that is closest to the designated electrode (or set of electrodes). A single step of a nearest neighbor search will find the neighboring relationship between two points (or in this application, two electrodes), which search is repeated in order to progressively find the neighboring relationship of the entire set of points (i.e., electrodes).

Figure 9:
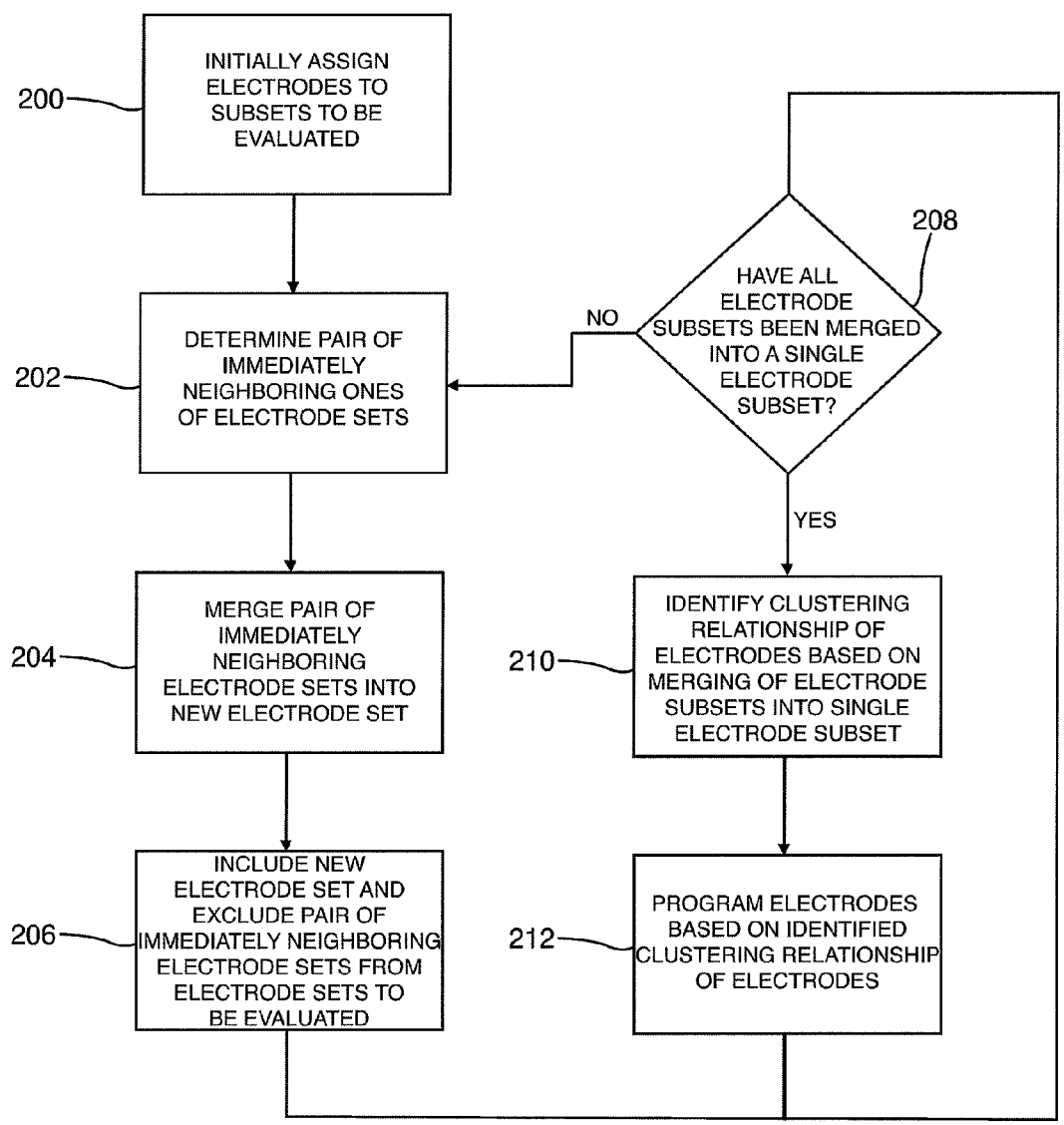
FIG. 9 is a flow diagram illustrated a generic method implemented by the SCS system of FIG. 1 to perform an electrode clustering analysis and program the electrodes.

To this end, and with reference to FIG. 9, the electrodes are initially assigned to a plurality of electrode subsets to be evaluated (step 200). In the illustrated embodiment, sixteen electrodes (electrodes E1-E16) are respectively assigned to sixteen electrode subsets (one electrode for each subset).

Next, a pair of immediately neighboring ones of the electrode subsets is determined (step 202). By way of example, two techniques can be used to determine the pair of immediately neighboring electrodes subsets, as will be described in further detail below. Each of these techniques can accomplish this step by determining relative proximities between pairs of the electrode subsets, and selecting the pair of electrode subsets that has the minimum relative proximity therebetween as the determined pair of immediately neighboring electrode subsets. As will be described in further detail below, selection of the pair of electrode subsets having the minimum relative proximity can be accomplished by determining the minimum electrode proximity between the respective pair of electrode subsets, the maximum electrode proximity between the respective pair of electrode subsets, or the average electrode proximity between the respective pair of electrode subsets.

As described above, determination of the relative proximity between electrodes can be accomplished by generating an electrical signal and measuring an electrical parameter (e.g., electrical field potential) between the electrodes in response to the electrical signal. Notably, because the electrodes are clustered based on the relative proximity between electrode subsets, there is no need to estimate the absolute proximity between electrodes. As such, an indirect measure of the relative proximity between electrodes would be sufficient. Monopolar electrical field potentials can be measured between any pair of electrodes (one used as a source of the electrical field potential that is returned to the IPG case 40, and the other used to measure the electrical field potential), with the value of the measured electrical field potentials being inversely related to the distance between the two electrodes. The field potential value can thus provide an indirect measure of the relative proximity between electrodes.

Next the determined pair of immediately neighbored electrodes subsets is merged into a new electrode subset that includes all electrodes in the pair of immediately neighboring electrode subsets (step 204), and then including the new electrode subset within the plurality of electrode subsets to be evaluated, while excluding the pair of immediately neighboring electrode subsets from the plurality of electrode sets to be evaluated (step 206). For example, if a first electrode subset {E1} and a second electrode subset {E2} are merged into a new electrode subset {E1, E2}, the new electrode subset {E1, E2} will be included in subsequent electrode evaluations, whereas the old electrode subsets {E1} and {E2} will be eliminated from subsequent electrode evaluations.

Next, steps 202-206 are repeated until all the electrode subsets have been merged into a single electrode subset, and in this case, until the sixteen electrode subsets {E1}-{E16} are merged into a single electrode subset {E1-E16} (step

208). Next, a clustering relationship of the electrodes is identified based at least in part on the incremental merging of the electrode subsets into the single electrode subset (step 210). As will be described in further detail below, identification of the clustering relationship of the electrodes will depend on the specific technique used to merge the electrode subsets together.

Next, the electrodes are programmed based on the identified clustering relationship of the electrodes (step 210). As examples, at least one electrode can be selected as a cathode and at least one other electrode can be selected as an anode based on the identified clustering relationship of the electrodes, as discussed above with respect to FIG. 8a, or groups of electrodes can be selected to create a respective plurality of stimulation regions based on the identified clustering relationship of the electrodes, as discussed above with respect to FIG. 8b. The CP 18 may automatically program the electrodes in response to the identification of the clustering relationship between the electrodes 26 and/or may display the clustering relationship between the electrodes 26 to the user, after which, the CP 18 may program the electrodes via user intervention (i.e., user manipulation of the interface of the CP 18 or RC 16).

As briefly discussed above, two exemplary techniques may be used to implement the generic electrode clustering method illustrated in FIG. 9.

In the first electrode clustering technique, an agglomerative algorithm is used in a hierarchical clustering analysis. This technique involves determining, as the pair of immediately neighboring electrode subsets determined in step 202, a pair of electrode subsets closest in proximity to each other than any other pair of electrode subsets is in proximity to each other, which is reiterated via step 208, and identifying the clustering relationship of the electrodes in step 210 by arranging the electrodes in hierarchical clustering structures. As an example, if there are N electrodes numbered as $E_1, E_2, \ldots E_N$, the agglomerative algorithm processes the clustering as follows.

Initially, each electrode is assigned to a single subset, i.e., $S_1=\{E_1\}, S_2=\{E_2\}, \ldots, S_N=\{E_N\}$, all of which are included in the subsets to be evaluated $S_{EVAL}$; that is, subsets under evaluation $S_{EVAL}=\{S_1, S_2, \ldots S_N\}$.

Next, the pair-wise distance/proximities between all possible combinations of two electrode subsets $d_{i,j}$, $i \neq j$ (e.g., $d_{1,2}$, $d_{1,3}, \ldots, D_{1,N}, d_{2,3}, \ldots, d_{N-1,N}$) is determined by implementing the minimum electrode proximity, the maximum electrode proximity, or the average electrode proximity techniques.

For the minimum electrode proximity technique, the following equation can be used to determine the pair-wise distance/proximity between given electrode subsets $S_i$, $S_j$:

$$d_{i,j} = \min_{E_x \in S_i, E_y \in S_j} (dist(E_x, E_y));$$

that is, the distance between a first given electrode subset $S_i$ and a second given electrode subset $S_j$ is the minimum pair-wise distance between all pair combinations of electrodes $E_x$, $E_y$, where $E_x$ is a member of electrode subset $S_i$, and $E_y$ is a member of electrode subset $S_j$.

For the maximum electrode proximity technique, the following equation can be used to determine the pair-wise distance/proximity between given electrode subsets $S_i$, $$S_j: d_{i,j} = \max_{E_x \in S_i, E_y \in S_j} (dist(E_x, E_y));$$

that is, the distance between a first given electrode subset $S_i$ and a second given electrode subset $S_j$ is the maximum pair-wise distance between all pair combinations of electrodes $E_x$, $E_y$, where $E_x$ is a member of electrode subset $S_i$, and $E_y$ is a member of electrode subset $S_j$.

For the average electrode proximity technique, the following equation can be used to determine the pair-wise distance/proximity between given electrode subsets $S_i$, $S_j$:

$$d_{i,j} = \frac{1}{K_i \times K_j} \sum_{E_x \in S_i} \sum_{E_y \in S_j} (dist(E_x, E_y));$$

that is, the distance between a first given electrode subset $S_i$ and a second given electrode subset $S_j$ is the average of the pair-wise distances between all possible pair combinations of electrodes $E_x$, $E_y$, where $E_x$ is a member of electrode subset $S_i$, $E_y$ is a member of electrode subset $S_j$, $K_i$ is the number of members in the electrode subset $S_i$, and $K_j$ is the number of members in the electrode subset $S_j$.

Next, the pair of electrode subsets $S_i$, $S_j$ that are closest to each other is identified; that is, find m,n such that $d_{m,n}$=min $(d_{i,j}, i \neq j)$. Then, the electrode subsets $S_m$, $S_n$ are merged into a new electrode subset $S_{NEW}=\{S_m, S_n\}$, which includes all members of electrode subsets $S_m$ and $S_n$. Next, the electrode subsets under evaluation $S_{EVAL}$ are updated to include the new electrode subset $S_{NEW}$, while excluding the merged electrode subsets $S_m$, $S_n$ from the electrode subsets under evaluation $S_{EVAL}$. The pair-wise distance/proximity determination, closest electrode subset pair determination, electrode subset merging, and electrode subset under evaluation updating steps are then repeated until all the electrodes have been merged into a single electrode subset.

Figure 10A:
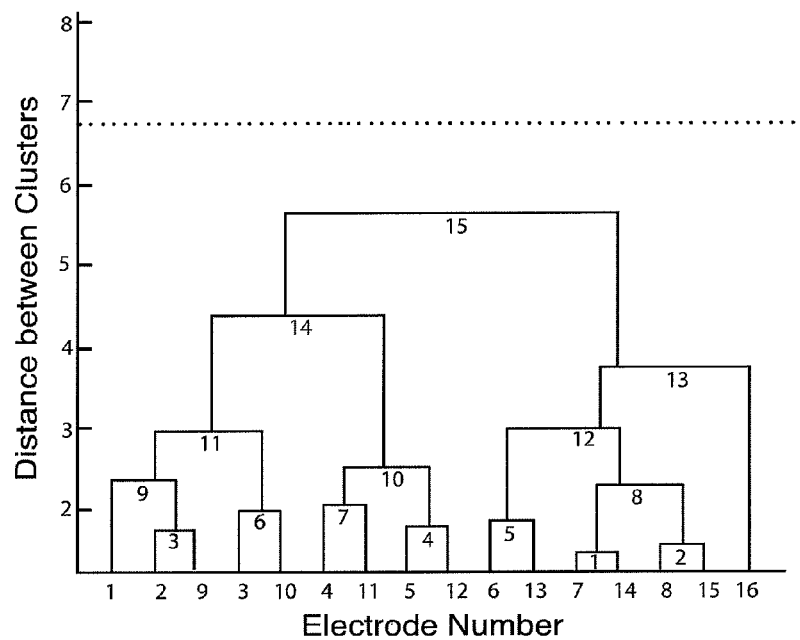
FIG. 10a is a dendrogram of a clustering analysis performed on the electrode arrangement of FIG. 8a using a first specific technique implemented by the SCS system of FIG. 1.
Figure 10B:
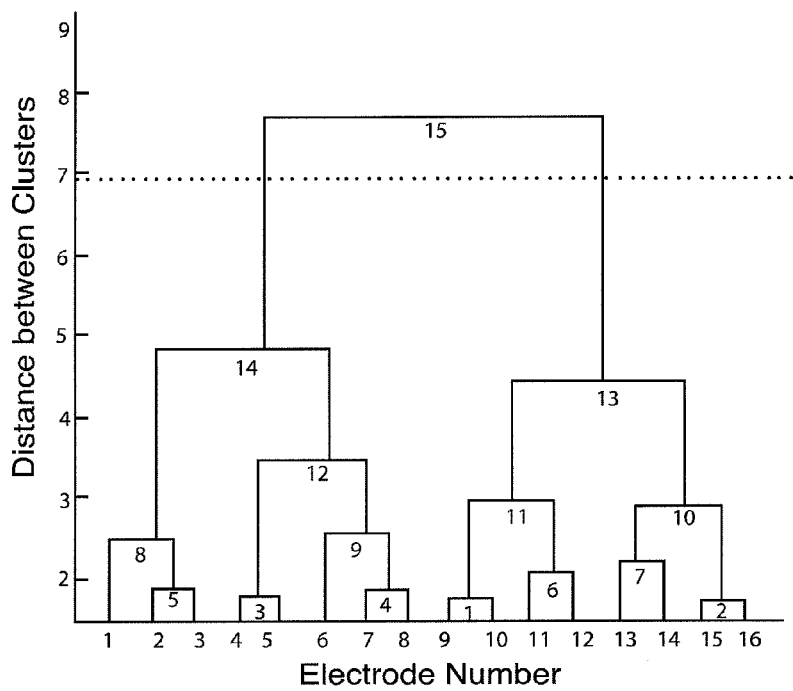
FIG. 10b is a dendrogram of a clustering analysis performed on the electrode arrangement of FIG. 8b using the first specific technique implemented by the SCS system of FIG. 1.
Figure 11A:
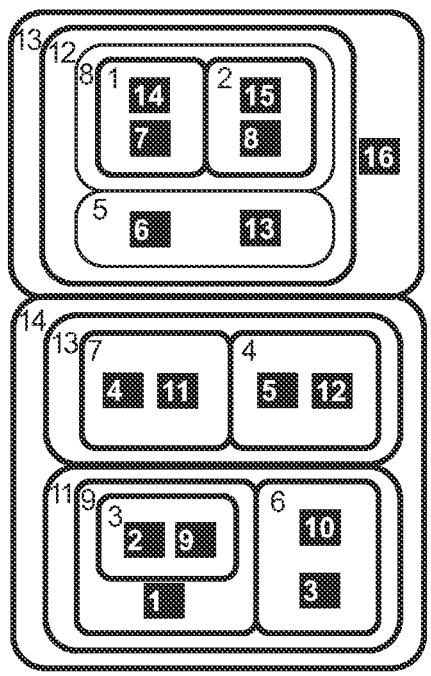
FIG. 11a is a partitioned block diagram of a clustering analysis performed on the electrode arrangement of FIG. 8a using the first specific technique implemented by the SCS system of FIG. 1.
Figure 11B:
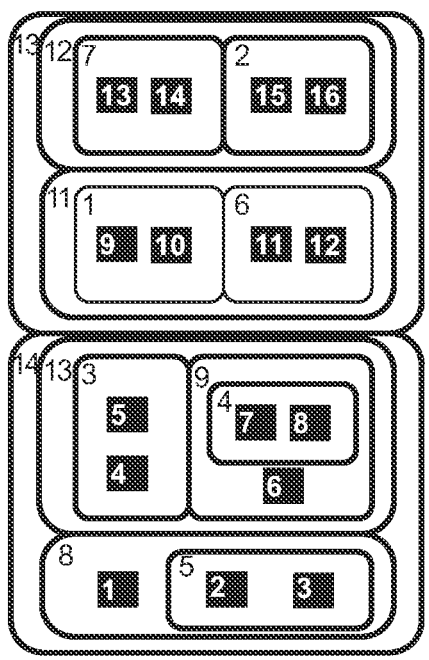
FIG. 11b is a partitioned block diagram of a clustering analysis performed on the electrode arrangement of FIG. 8b using the first specific technique implemented by the SCS system of FIG. 1.

As briefly discussed above, the agglomerative algorithm can be used to identify the clustering relationship of the electrodes by arranging the electrodes in hierarchical clustering structures. For example, given the electrode arrangements illustrated in FIGS. 8a and 8b, dendrograms representing the clustering structures of the electrodes can be generated, as respectively illustrated in FIGS. 10a and 10b, or partitioned block diagrams representing the clustering structures of the electrodes can be generated, as respectively illustrated in FIGS. 11a and 11b. Each of the dendrograms illustrated in FIGS. 10a and 10b starts from the root, which consists of a single cluster containing all electrodes, and is branched from top to bottom to illustrate the merging relationship. Similarly, each of the partitioned block diagrams illustrated in FIGS. 11a and 11b contains boxes that are successively partitioned to illustrate the merging relationship.

Figure 8A:
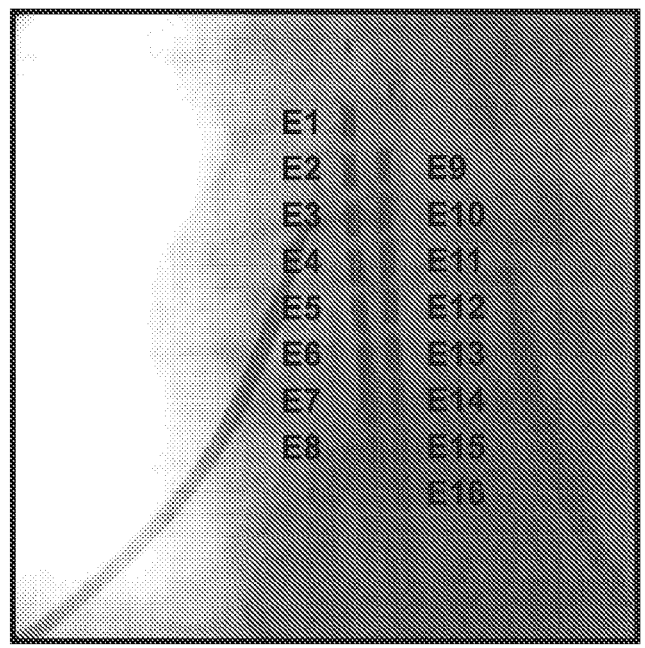
FIG. 8a is a fluoroscopic image of a clinical case wherein neurostimulation leads are implanted within a patient in a side-by-side relationship.

With respect to the electrode arrangement in FIG. 8a, a review of these dendrograms and partitioned block diagrams reveals that the electrode subsets {E2, E9}, {E3, E10}, {E4, E11}, {E5, E12}, {E6, E13}, {E7, E14}, {E8, E15} can be identified as two-electrode clusters; the electrode subset {E1, E2, E9} can be identified as a three-electrode cluster; the electrode subsets {E4, E5, E11, E12} and {E7, E8, E14, E15} can be identified as four-electrode clusters; the electrode subset {E1-E3, E9, E10} can be identified as a five-electrode cluster; the electrode subset {E6-E8, E13-E15} can be identified as a six-electrode cluster; the electrode subset {E6-E8, E13-E16} can be identified as a seven-electrode cluster; and the electrode subset {E1-E5, E9-E12} can be identified as a nine-electrode cluster. Thus, variously sized electrode clusters, which are mapped to the electrodes, can be easily programmed as anodes or cathodes.

Figure 8B:
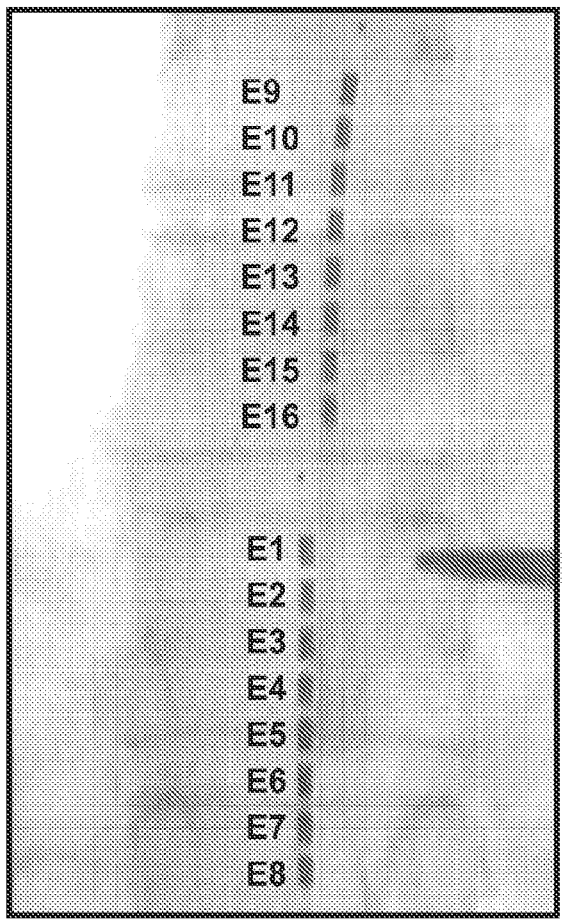
FIG. 8b is a fluoroscopic image of a clinical case wherein neurostimulation leads are implanted within a patient in rostro-caudal relationship.

With respect to the electrode arrangement in FIG. 8b, a review of these dendrograms and partitioned block diagrams reveals that the electrode subset {E1-E8} are located in one anatomical region, and the electrode subset {E9-E16} are located in another anatomical region. Thus, two electrode clusters, which are mapped to the electrodes, can be easily respectively programmed to create two stimulation regions.

In the second electrode clustering technique, an algorithm is used in a cluster ordering analysis. This technique involves including the new electrode subset and a single electrode closest in proximity to the new electrode subset within the pair of immediately neighboring electrode subsets subsequently determined in step 202, which is reiterated via step 208, and identifying the clustering relationship of the electrodes in step 210 by arranging the single electrodes in an order in which they are included within the pair of immediately neighboring electrode subsets. As an example, if there are N electrodes numbered as $E_1, E_2, \ldots E_N$, this algorithm processes the clustering as follows.

Initially, each electrode is assigned to a single subset, i.e., $S_1=\{E_1\}, S_2=\{E_2\}, \ldots, S_N=\{E_N\}$, all of which are included in the subsets to be evaluated $S_{EVAL}$; that is, subsets under evaluation $S_{EVAL}=\{S_1, S_2, \ldots, S_N\}$. Next, one of the subsets is selected as the present subset $S_{PRES}$ into which all subsequent single electrode subsets $S_j$ will eventually be merged, as will be discussed in further detail below.

Then, the pair-wise distance/proximities between all possible combinations of the present subset $S_{PRES}$ and the remaining single-electrode subsets $S_j$ (i.e., $S_j \in S_{PRES}$) are determined by implementing the minimum electrode proximity, the maximum electrode proximity, or the average electrode proximity techniques.

For the minimum electrode proximity technique, the following equation can be used to determine the pair-wise distance/proximity between the present electrode subset $S_{PRES}$ and a remaining single-electrode subset $S_j$:

$$d_j = \min_{E_x \in S_{PRES}} (dist(E_x, E_y));$$

that is, the distance between the present subset $S_{PRES}$ and the single-electrode subset $S_j$ is the minimum pair-wise distance between all pair combinations of electrodes $E_x, E_y$, where $E_x$ is a member of electrode subset $S_{PRES}$, and $E_y$ is the only member of electrode subset $S_j$.

For the maximum electrode proximity technique, the following equation can be used to determine the pair-wise distance/proximity between the present electrode subset $S_{PRES}$ and a remaining single-electrode subset $S_j$:

$$d_j = \max_{E_x \in S_{PRES}} (dist(E_x, E_y));$$

that is, the distance between the present subset $S_{PRES}$ and the single-electrode subset $S_j$ is the maximum pair-wise distance between all pair combinations of electrodes $E_x, E_y$, where $E_x$ is a member of electrode subset $S_{PRES}$, and $E_y$ is the only member of electrode subset $S_j$.

For the average electrode proximity technique, the following equation can be used to determine the pair-wise distance/proximity between the present electrode subset $S_{PRES}$ and a remaining single-electrode subset $S_j$:

$$d_j = \frac{1}{K} \sum_{E_x \in S_{PRES}} dist(E_x, E_y);$$

that is, the distance between the present subset $S_{PRES}$ and the single-electrode subset $S_j$ is the average of the pair-wise distances between all possible pair combinations of electrodes $E_x, E_y$, where $E_x$ is a member of present electrode subset $S_{PRES}$, $E_y$ is the only member of electrode subset $S_j$, and K is the number of members in the present electrode subset $S_{PRES}$.

Next, the single-electrode subset $S_i$ that is closest to the present electrode subset $S_{PRES}$ is identified; that is, find n such that $d_n = \min(d_j)$. Then, the present electrode subset $S_{PRES}$ and the single-electrode subset $S_n$ are merged into a new electrode subset $S_{NEW} = \{S_{PRES}, S_n\}$, which includes all members of the present electrode subset $S_{PRES}$ and the single electrode subset $S_n$. Optionally, the pair-wise distance/proximity between the newly merged single electrode subset $S_n$ and each of the existing electrodes in the present electrode subset $S_{PRES}$ is assessed and sorted (i.e., $dist(E_n, E_i)$ for $E_i \in S_{PRES}$. The two electrodes in the present electrode subset $S_{PRES}$ that are closest to the newly merged single electrode subset $S_n$ provides an estimate of the direction in which the merged single electrode subset $S_n$ is relative to the present electrode subset $S_{PRES}$.

Next, the electrode subsets under evaluation $S_{EVAL}$ are updated to include the new electrode subset $S_{NEW}$, while excluding the merged electrode subsets $S_{PRES}$, $S_n$ from the electrode subsets under evaluation $S_{EvAL}$. The new electrode subset $S_{NEW}$ is then used as the next present electrode subset $S_{PRES}$. The pair-wise distance/proximity determination, closest electrode subset pair determination, electrode subset merging, and electrode subset under evaluation updating steps are then repeated until all the electrodes have been merged into a single electrode subset.

As briefly discussed above, this algorithm can be used to identify the clustering relationship of the electrodes by arranging the electrodes in an order in which they are included within the pair of immediately neighboring electrode subsets.

Figure 12A:
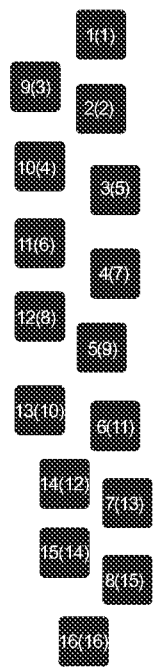
FIG. 12a is a plot of a clustering analysis performed on the electrode arrangement of FIG. 8a using a second specific technique implemented by the SCS system of FIG. 1.
Figure 12B:
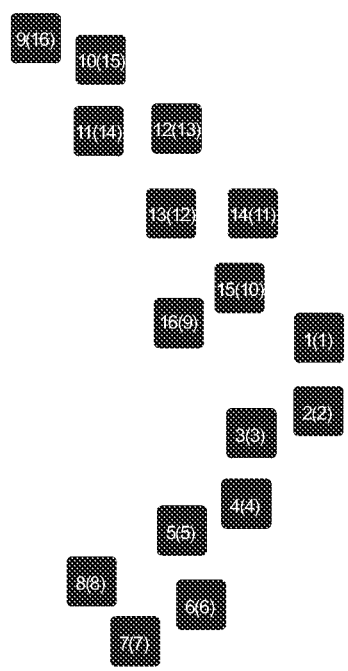
FIG. 12b is a plot of a clustering analysis performed on the electrode arrangement of FIG. 8b using the second specific technique implemented by the SCS system of FIG. 1.

For example, given the electrode arrangements illustrated in FIGS. 8a and 8b, the clustering order of the electrodes can be illustrated by successively plotting an electrode next to its nearest neighbor in the order of merging, as respectively illustrated in FIGS. 12a and 12b. The numbers in parentheses next to the electrode numbers indicate the order of merging. It should be noted that the plots of the electrode arrays may not faithfully represent two linear leads, because the electrode position relative to its nearest neighbor is determined solely by the relative distances between the electrodes, and the algorithm does not assume a linear electrode arrangement. The electrode array plot illustrated in FIG. 12a looks more linear because the position of each electrode in this case was determined from two immediately adjacent neighbors (one in the longitudinal direction and one in the lateral direction), while the electrode array plot illustrated in FIG. 12b are carried by two separated leads and the position of each electrode was determined from two in-line neighbors (one of them not being immediately adjacent) without making a linear electrode array assumption.

A review of the electrode arrangement in FIG. 12a reveals that any electrode and its neighboring electrodes can be selected to form any sized cluster. For example, electrode E4 and its neighboring electrodes E3, E5, E11, and E12 can be selected to form a five-electrode cluster; or electrode E1 and its neighboring electrodes E2 and E9 can be selected to form a three-electrode cluster, etc. Thus, variously sized electrode clusters, which are mapped to the electrodes, can be easily programmed as anodes or cathodes.

A review of the electrode arrangement in FIG. 12b reveals that electrodes E1-E8 are located in one anatomical region, and the electrodes E9-E16 are located in another anatomical region. Thus, two electrode clusters, which are mapped to the electrodes, can be easily respectively programmed to create two stimulation regions.

While the foregoing electrode clustering techniques provide a good estimate of the relative proximities between the electrodes, it may be desirable to provide a more accurate representation of the electrode array, so that, e.g., the electrodes can be mapped to different linear electrode configurations that are closely spaced from each other.

Figure 13A:
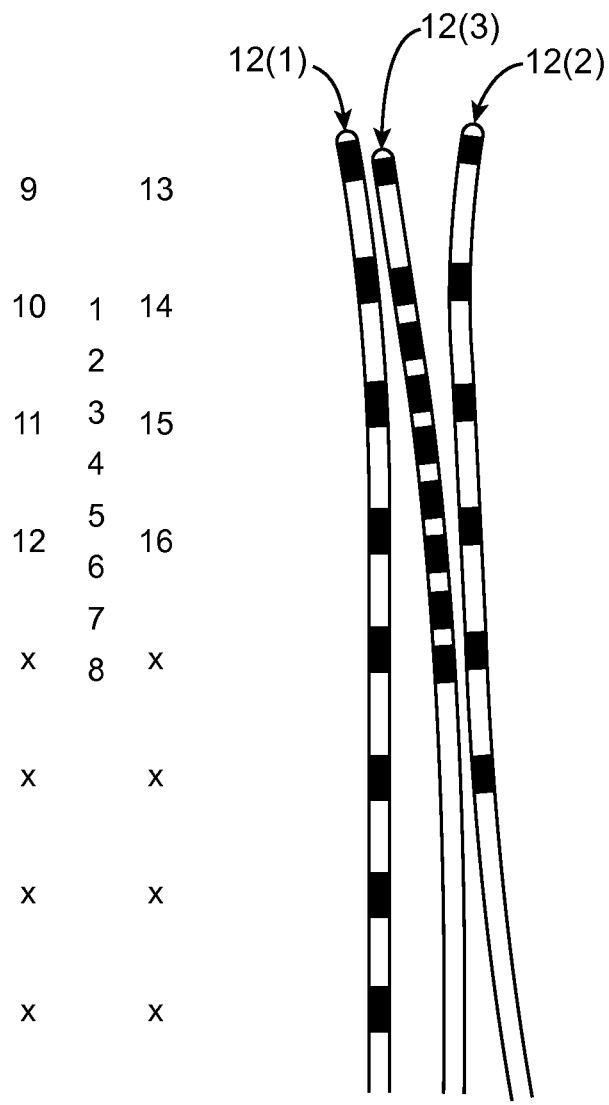
FIG. 13a is an image of illustrating a first configuration of three neurostimulation leads are implanted within a patient in a side-by-side relationship.
Figure 13B:
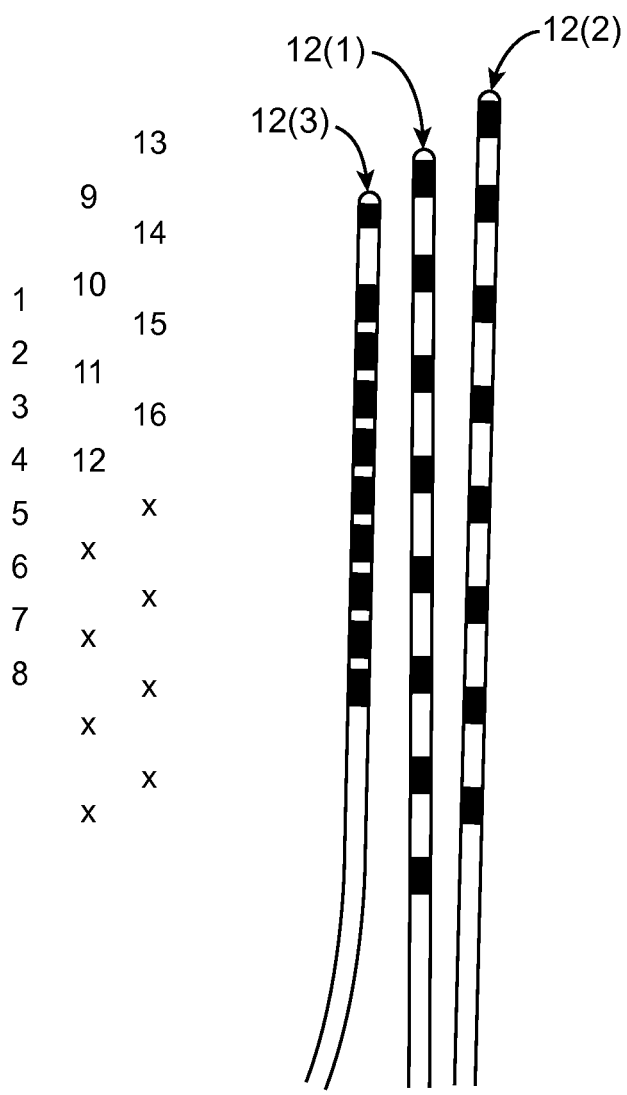
FIG. 13b is an image of illustrating a second configuration of three neurostimulation leads are implanted within a patient in a side-by-side relationship.

For example, each of FIGS. 13a and 13b illustrates three neurostimulation leads 12(1)-12(3) arranged in a parallel relationship, with each of the first two leads 12(1), 12(2) having relatively large electrode spacings, and the third lead 12(3) having relatively small electrode spacings. In FIG. 13a, the third lead 12(3) is located between the leads 12(1), 12(2), whereas in FIG. 13b, the third lead 12(3) is located on the left of the leads 12(1), 12(2). The numbers 1-16 illustrated on the left side of the leads 12 spatially correspond to the active electrodes E1-E16 carried by the leads 12, whereas the X's correspond to inactive electrodes carried by the leads.

In both cases, the leads 12(1), 12(2) are connected to one connector port on the IPG 14 via a splitter (not shown), and the lead 12(3) is connected to the other connector port on the IPG 14 without the use of a splitter, such that electrodes E1-E8 on lead 12(3) are coupled to one connector port, and electrodes E9-E12 at the distal end of the lead 12(1) and electrodes E13-E16 at the distal end of the lead 12(2) are coupled to the other connector port. In effect, one 1×8 electrode array and two 1×4 electrode arrays have been created using the splitter, although the IPG 14 has been designed to support two 1×8 electrode arrays. Without prior knowledge of how the splitter is used to couple the leads 12 to the IPG 14, the CP 18 is capable of identifying the actual electrode positions relative to each other and mapping the nominal electrodes E1-E16 to these actual electrode positions, as will now be discussed.

Using electrode neighbor information obtained using a suitable technique, such as, e.g., the second electrode clustering technique described above, this method generates a map indicating the positions of all electrodes in accordance with a set of rules that presupposes that the electrodes are arranged in linear arrays. This is accomplished by placing neighbor electrodes within a spatial grid of electrode positions based on its relationship to a designated reference electrode and other neighbor electrodes surrounding the same reference electrode.

Placement of the electrodes in the grid is accomplished in an iterative fashion to gradually expand the electrode map in that once the first reference electrode and its neighbor electrodes are placed in the grid, one of the neighbor electrodes of the first reference electrode will be used as a second reference electrode to position the neighbor electrodes of the second reference electrode that have not already been positioned within the grid, then one of the neighbor electrodes to the second reference electrode will be used as the third reference electrode to position the neighbor electrodes of the third reference electrode that have not already been positioned within the grid, and so forth until all of the electrodes are positioned in the grid.

Figure 14:
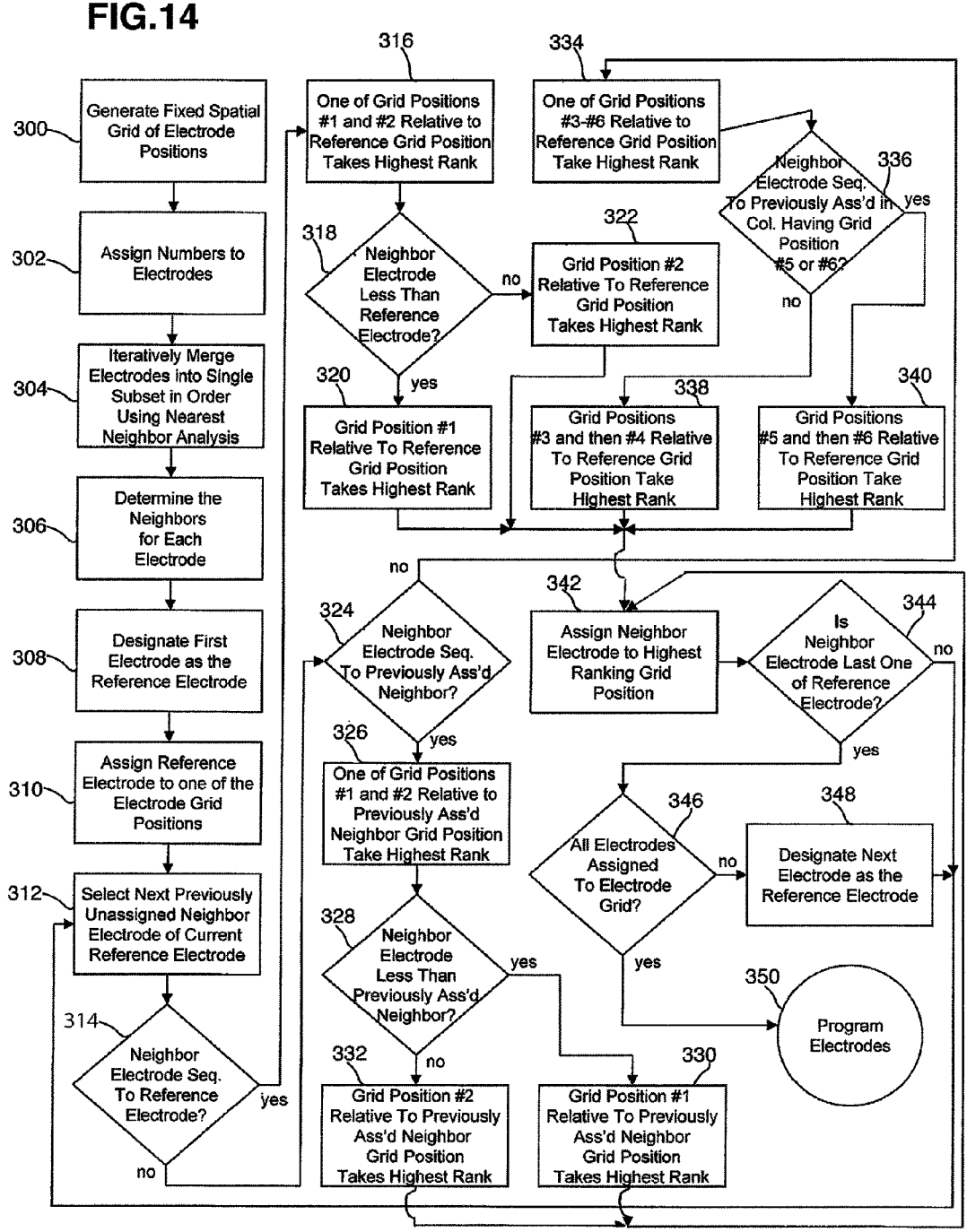
FIG. 14 is a flow diagram illustrated a generic method implemented by the SCS system of FIG. 1 to perform an electrode configuration mapping technique and program the electrodes.
Figure 15:
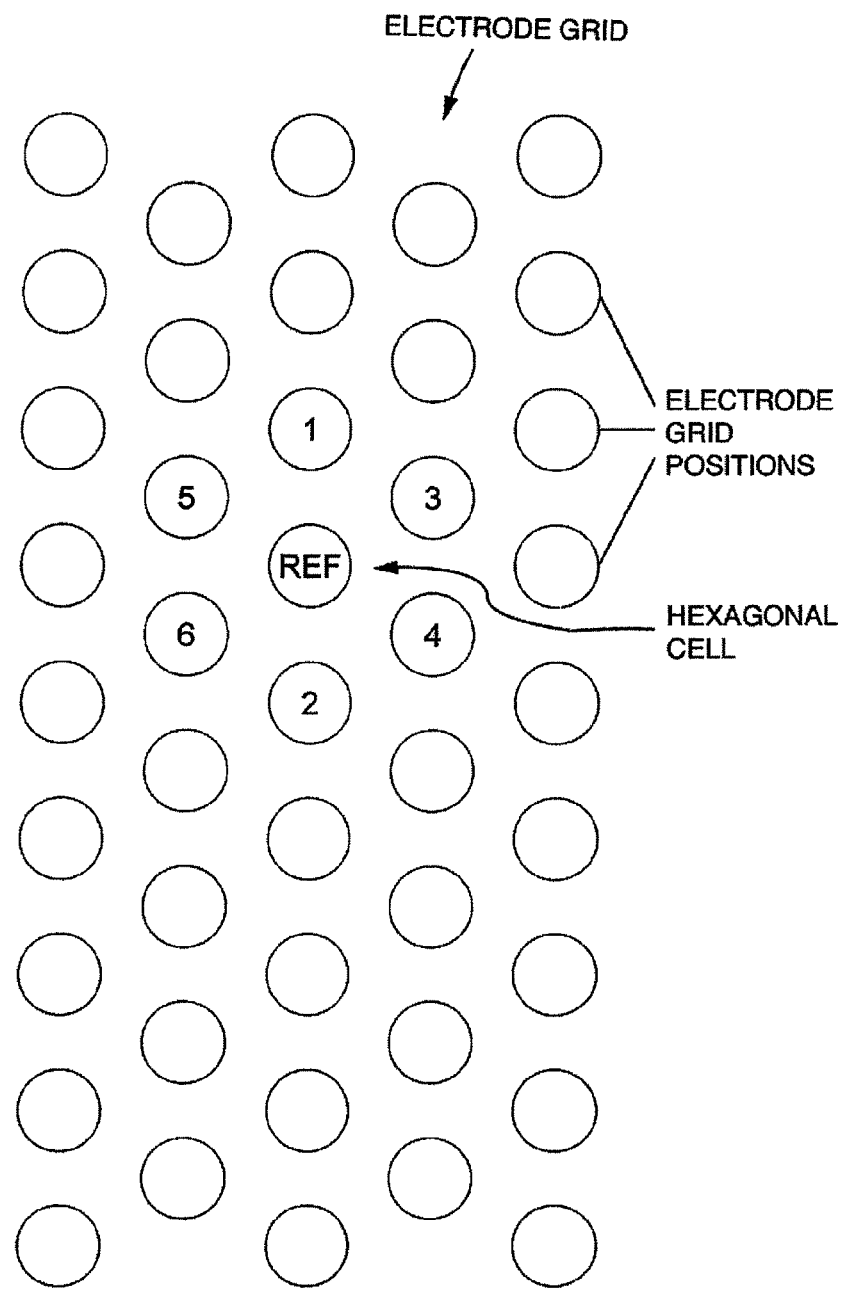
FIG. 15 is a plan view of a spatial grid of electrode positions generated by the SCS system of FIG. 1 to which electrodes will be assigned in accordance with the electrode configuration mapping technique performed in FIG. 14.

To this end, and with reference to FIG. 14, a fixed spatial grid of electrode positions (represented by circles) is generated (step 300), as illustrated in FIG. 15. As there shown, the electrode grid positions are arranged in columns representing linear arrays of electrodes. Preferably, the number of columns and number of grid positions in each column are at least equal to the contemplated number of leads and number of active electrodes carried by each lead that will be used in the neurostimulation system 10. As illustrated in FIG. 15, the electrode grid can be divided into hexagonal cells, with each cell having a reference electrode grid position (labeled REF) and six electrode grid positions (numbered 1-6) immediately surrounding the reference grid position. Alternatively, the electrode grid can be divided into other polygonal shapes, such as octagons, quadrangles, etc. Although only one of the grid positions is shown as a reference grid position, any of the grid positions can be designated as a reference grid position, as will be described in further detail below. Because this technique is only concerned with the relative positions between the electrodes, the variation in distance among the neighbor electrodes to the reference electrode, which may arise from the variation in lead type, lead separation, noise level, etc. can be ignored, and thus, the spacings between the grid positions are fixed and uniformly spaced.

Next, different numbers are initially assigned to all of the electrodes that are to be placed into the electrode grid (step 302). Preferably, the numbers are assigned to the electrodes based on a conventional mapping between the connector port terminals and the respective electrodes. For example, if there are two connector ports that are conventionally coupled to two 1×8 electrode arrays (as in the present case), connector terminals 1-8 correspond to electrodes E1-E8, and connector terminals correspond to electrodes E9-E16. Thus, the electrodes will be designated E1-E16 in accordance to the connector terminals to which they are coupled. In the illustrated embodiment, the numbers 1-16 are respectively assigned to sixteen electrodes, as illustrated in FIGS. 13a and 13b. It should be noted that the CP 18 does not know, at this point, the physical configuration of the electrodes E1-E16 shown in FIGS. 13a and 13b. The CP 18 only knows the assigned number of the electrode that is coupled to any particular connector terminals.

As will be described in further detail below, each electrode will be iteratively designated a reference electrode that will be placed, along with its neighboring electrodes, in the electrode grid in a specific order. In the illustrated embodiment, the specific order in which each electrode is designated a reference electrode is determined in accordance with the clustering order of the electrodes determined using the second electrode clustering technique described above. That is, each electrode is iteratively merged into a single electrode subset in an order dictated by a nearest neighbor analysis (i.e., by merging the electrode closest in proximity to the single electrode subset) for each iteration (step 304). This merging order will be the order in which each electrode is designated a reference electrode with respect to the electrode grid. Next, for each electrode, neighboring ones of the remaining electrodes are determined (step 306), e.g., by analyzing the pairwise proximities between the electrodes acquired during the electrode merging steps of the second electrode clustering technique.

The electrode clustering analysis performed in steps 304 and 306 may yield a table-like data array that lists the electrodes in the order of merging in one column (reference electrode column), and up to six neighbor electrodes identified as the nearest neighbors (Neighbor N1-N6 columns) to the respective reference electrode.

Tables 1a and 1b below provide the list of the electrodes (in their merging order) and their nearest neighbor electrodes for the two example cases illustrated in FIGS. 13a and 13b, respectively. Each table is generated by first populating the reference electrode column with the electrodes in the order that they are merged into the single subset of electrodes. For each reference electrode, the two closest neighbors are determined from the pair-wise proximity measurements obtained during the electrode clustering technique, which are then filled into the locations in the neighbor N1 and neighbor N2 columns corresponding to the respective reference electrode.

To the extent that one of two nearest neighbors for a currently identified reference electrode has previously been identified as a reference electrode in the table, the currently identified reference electrode is backfilled into the next available neighbor electrode column (N3-N6) in the row of the table corresponding to the previously identified reference electrode. Notably, due to inherent noise in the proximity measurements, the two nearest neighbors of the respective reference electrode may not necessarily match the actual two nearest neighbors of the respective reference electrode. It should also be noted that electrode E12 is not listed in Table 1a, because there was an open circuit in the electrode when taking the proximity measurements. However, if it is known that electrode E12 is in use, due to the redundancy built in the tables, electrode E12 can still be properly placed within the electrode array, as evidenced below.

TABLE 1a (Electrodes in Order of Merging and Nearest Neighbors for Case #1)

| Reference Electrode | Neighbor N1 | Neighbor N2 | Neighbor N3 | Neighbor N4 | Neighbor N5 | Neighbor N6 |
|---|---|---|---|---|---|---|
| 7 | 8 | 6 | 16 | — | — | — |
| 8 | 7 | 6 | — | — | — | — |
| 6 | 7 | 8 | 16 | 5 | 4 | — |
| 16 | 6 | 7 | 5 | — | — | — |
| 5 | 6 | 16 | 4 | 3 | — | — |
| 4 | 5 | 6 | 3 | 15 | 11 | — |
| 3 | 4 | 5 | 15 | 11 | 2 | 1 |
| 15 | 3 | 4 | — | — | — | — |
| 11 | 3 | 4 | 2 | — | — | — |
| 2 | 3 | 11 | 1 | 10 | 14 | — |
| 1 | 2 | 3 | 10 | 14 | 9 | — |
| 10 | 1 | 2 | 9 | — | — | — |
| 14 | 1 | 2 | 13 | — | — | — |
| 9 | 10 | 1 | 13 | — | — | — |
| 13 | 9 | 14 | — | — | — | — |

TABLE 1b (Electrodes in Order of Merging and Nearest Neighbors for Case #2)

| Reference Electrode | Neighbor N1 | Neighbor N2 | Neighbor N3 | Neighbor N4 | Neighbor N5 | Neighbor N6 |
|---|---|---|---|---|---|---|
| 8 | 7 | 6 | — | — | — | — |
| 7 | 8 | 6 | 5 | — | — | — |
| 6 | 7 | 8 | 5 | 4 | — | — |
| 5 | 6 | 7 | 4 | 3 | — | — |
| 4 | 5 | 6 | 3 | 12 | — | — |
| 3 | 4 | 5 | 12 | 2 | 11 | — |
| 12 | 3 | 4 | 16 | 2 | — | — |
| 2 | 3 | 12 | 11 | 1 | — | — |
| 11 | 2 | 3 | 1 | 16 | 15 | 10 |
| 1 | 11 | 2 | — | — | — | — |
| 16 | 12 | 11 | 15 | — | — | — |
| 15 | 16 | 11 | 10 | 14 | — | — |
| 10 | 15 | 11 | 14 | 9 | — | — |

TABLE 1b-continued (Electrodes in Order of Merging and Nearest Neighbors for Case #2)

| Reference Electrode | Neighbor N1 | Neighbor N2 | Neighbor N3 | Neighbor N4 | Neighbor N5 | Neighbor N6 |
|---|---|---|---|---|---|---|
| 14 | 10 | 15 | 9 | 13 | — | — |
| 9 | 14 | 10 | 13 | — | — | — |
| 13 | 9 | 14 | — | — | — | — |

After the electrode merging/neighbor table has been generated, the first electrode in the table is designated as a reference electrode to be currently examined (step 308), which is then assigned to one of the electrode grid positions (step 310). Next, one or more previously unassigned ones of the electrodes neighboring the reference electrode are respectively assigned to one or more of the electrode grid positions immediately surrounding the current reference grid position (steps 312-344).

In the illustrated embodiment, the neighbor electrodes are assigned to the neighbor grid positions surrounding the reference grid position in accordance with a set of rules that distinguishes between electrodes that are in-line with the reference electrode and electrodes that are off-line with the reference electrode.

To this end, the next previously unassigned neighbor electrode of the reference electrode is currently selected for assignment within the electrode grid (step 312). In the illustrated embodiment, the currently selected neighbor electrode will be the next numbered neighbor electrode of the reference electrode, as listed in the merging order/neighbor table. That is, if neighbor electrode N1 has previously been assigned to the electrode grid, and neighbor electrode N2 has not been previously been assigned to the electrode grid, then neighbor electrode N2 will be currently selected for assignment within the electrode grid. Of course, if no neighbor electrodes relative to the currently reference electrode have been assigned to the electrode grid, then the first neighbor electrode N1 will be initially selected.

Next, one of the neighbor grid positions is ranked based on the likelihood of the currently selected neighbor electrode being in-line or off-line with the reference electrode (steps 314-340). In particular, each of the six neighbor grid positions takes a different priority when assigning each neighbor electrode within the electrode grid.

Because the electrode grid positions are spatially arranged in columns respectively representing linear arrays of electrodes, the neighbor grid positions around the reference grid position can be prioritized based on what column they are likely in relative to the reference grid position. For example, grid positions #1 and #2 (same column in which the reference grid position is) will take priority when assigning neighbor electrodes that are likely carried by the same lead as the reference electrode; grid positions #3 and #4 (column to the right of the column in which the reference grid position is) will take priority when assigning neighbor electrodes that are likely carried by a lead that is different from the lead carrying the reference electrode; and grid positions #5 and #6 (column to the left of the column in which the reference grid position is) will take priority when assigning neighbor electrodes that are likely carried by a third lead that is different from the leads carrying the reference electrode and the lead carrying electrodes assigned to grid positions #3 and #4. The currently selected neighbor electrode will be assigned to the open neighbor position having the highest priority.

In particular, if the electrode number of the currently selected neighbor electrode is sequential to the electrode number of the reference electrode at a threshold (step 314), the neighbor electrode is likely in-line with the reference electrode, and thus, grid positions #1 and #2 relative to the reference grid position take the highest rank (step 316). In the illustrated embodiment, the threshold is one, such that electrode numbers are sequential only if their difference is one (e.g., electrode E2 is sequential to electrode E3, but not sequential to electrode E4). If the threshold is increased to, e.g., two (which may be preferable if the proximity measurements are anticipated to be noisy), the electrodes numbers are sequential only if their difference is two or less (e.g., electrode E2 is sequential to electrodes E3 or E4).

The rank of grid position #1 versus grid position #2 depends on the sign of the difference in the electrode numbers of the neighbor electrode and reference electrode. In the illustrated embodiment, if the number of the neighbor electrode is less than the number of the reference electrode (step 318), grid position #1 is ranked over grid position #2, and thus, takes the highest rank (step 320); otherwise, grid position #2 is ranked over grid position #1, and thus, takes the highest rank (step 322). Alternatively, if the number of the neighbor electrode is greater than the number of the reference electrode, grid position #1 is ranked over grid position #2; otherwise, grid position #2 is ranked over grid position #1. Ultimately, it does not matter which of the grid positions #1 or #2 ranks highest with respect to the sign of difference between the electrode numbers, as long as all the neighbor electrodes are assigned to the electrode grid positions in accordance with the same rule.

If the number of the currently selected neighbor electrode currently is not sequential with the number of the reference electrode at the threshold (step 314), but rather is sequential to the number of a neighbor electrode that has previously been assigned to the electrode grid with respect to the reference electrode at the threshold (step 324), the currently selected neighbor electrode is likely in-line with the previously assigned neighbor electrode, and thus, grid positions #1 and #2 relative to the grid position corresponding to the previously assigned neighbor electrode take the highest rank (step 326). Again, the rank of grid position #1 versus grid position #2 depends on the sign of the difference in the electrode numbers of the currently selected neighbor electrode and previously assigned neighbor electrode. In the illustrated embodiment, if the electrode number of the currently selected neighbor electrode is less than the electrode number of the previously assigned electrode (step 328), grid position #1 is ranked over grid position #2, and thus, takes the highest rank (step 330); otherwise, grid position #2 is ranked over grid position #1, and thus, takes the highest rank (step 332).

If the number of the currently selected neighbor electrode is not sequential with the number of the reference electrode or the number of a neighbor electrode previously assigned to the electrode grid with respect to the reference electrode (step 324), grid positions #3-#6 relative to the reference grid position are ranked the highest (step 334). If the number of the currently selected neighbor electrode is not sequential with the number of any electrode that has previously been assigned to grid positions in the same column as grid positions #5 or #6 relative to the reference grid position (step 336), grid positions #3 and #4 relative to the reference grid position ranks the highest (step 338), and positions #5 and #6 relative to the reference grid position rank the highest otherwise (step 340). As a general rule, position #3 ranks higher than position #4, and position #5 ranks higher than position #6.

Once the grid positions are ranked (steps 320, 322, 338, 340), the currently selected neighbor electrode is assigned to the highest ranking grid position (step 342). If the currently selected neighbor electrode is not the last neighbor electrode of the reference electrode currently under examination (step 344), the next neighbor electrode of the reference electrode is selected and assigned to the appropriate electrode grid position in accordance with steps 312-342. If the currently selected neighbor electrode is the last neighbor electrode of the reference electrode currently under examination (step 344), and if not all of the electrodes have been assigned to the electrode grid (step 346), the next electrode in the table, which will have already been assigned to the electrode grid, is designated as a reference electrode to be currently examined (step 348), and previously unassigned ones of the electrodes neighboring the reference electrode are respectively assigned to the electrode grid positions immediately surrounding the grid position to which the reference electrode is assigned (steps 312-344).

Figure 16A:
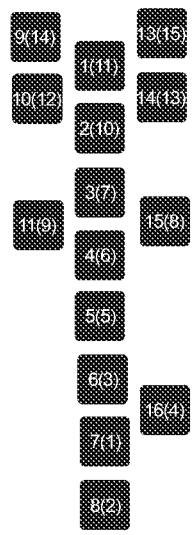
FIG. 16a is a plan view of an electrode configuration map of the neurostimulation lead configuration of FIG. 13a estimated by the SCS system of FIG. 1 in accordance with the technique performed in FIG. 14.
Figure 16B:
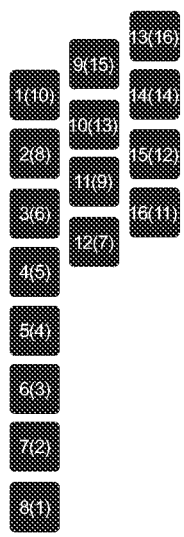
FIG. 16b is a plan view of an electrode configuration map of the neurostimulation lead configuration of FIG. 13b estimated by the SCS system of FIG. 1 in accordance with the technique performed in FIG. 14.

After all of the electrodes have been assigned to the electrode grid, a rough map of the electrodes can be obtained, and the electrodes can be programmed (step 350). For example, the electrode maps illustrated in FIGS. 16a and 16b, which show electrode configurations along with the order in which the electrodes are merged in parentheses, can be obtained by applying the technique provided in FIG. 14 to Tables 1a and 1b, which were obtained from the electrode configuration cases illustrated in FIGS. 13a and 13b.

As one example, and with reference to FIG. 17a-17h, the assignment of electrodes of the configuration illustrated in FIG. 13a to the electrode grid will now be discussed. For clarity, the bolded circle in each iteration described with respect to FIGS. 17a-17h represents the reference electrode grid position.

Figure 17A:
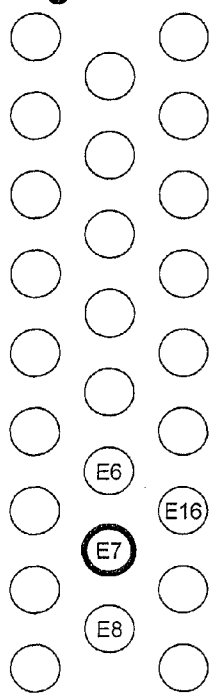
FIGS. 17a-17h are plan views illustrating the iterative assignment of electrodes from the neurostimulation lead configuration of FIG. 13a to the electrode grid of FIG. 15 by the SCS system of FIG. 1 in accordance with the technique performed in FIG. 14.

Electrode E7, which is the first listed reference electrode in Table 1a, is designated as the reference electrode to be currently examined, and is then assigned to a reference grid position (FIG. 17a). Electrode E8, as the first neighbor electrode to electrode E7, is assigned to grid position #2 relative to the current reference grid position, since electrode E8 is sequential to, and has a higher number than, electrode E7. Electrode E6, as the second neighbor electrode to electrode E7, is assigned to grid position #1 relative to the current reference grid position, since electrode E6 is sequential to, and has a lower number than, electrode E7. Electrode E16, as the third neighbor electrode to electrode E7, is assigned to grid position #3 relative to the current reference grid position, since electrode E16 is not sequential to electrode E7 or the other two previously assigned neighbor electrodes E6 and E8, and no other electrode has been previously assigned to a grid position in the same column in which grid positions #5 or #6 relative to the current reference grid position are located.

Electrode E8, which is the second listed reference electrode in Table 1a, does not have any neighbor electrodes that have not been previously assigned to the electrode grid, and therefore, is not designated as a reference electrode for current examination.

Figure 17B:
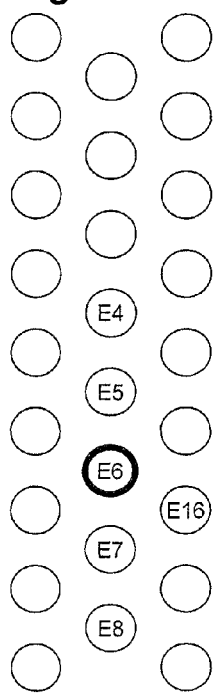

Electrode E6, which is the third listed reference electrode in Table 1a, is designated as the reference electrode to be currently examined, since it does have at least one neighbor electrode that has not been previously assigned to the electrode grid, in which case, the grid position that electrode E6 was previously assigned to is designated as the current reference grid position (FIG. 17b). Electrode E5, as the fourth and next unassigned neighbor electrode to electrode E6, is assigned to reference position #1 relative to the current reference grid position, since electrode E5 is sequential to, and has a lower number than, electrode E6. Electrode E4, as the fifth and next unassigned neighbor electrode to electrode E6, is assigned to grid position #1 relative to the grid position to which electrode E5 is assigned, since electrode E4, while not sequential to electrode E6, is sequential to, and a lesser number than, electrode E5, a neighbor electrode previously assigned to the electrode grid relative to the current reference grid position.

Electrode E16, which is the fourth listed reference electrode in Table 1a, does not have any neighbor electrodes that have not been previously assigned to the electrode grid, and therefore, is not designated as a reference electrode for current examination.

Figure 17C:
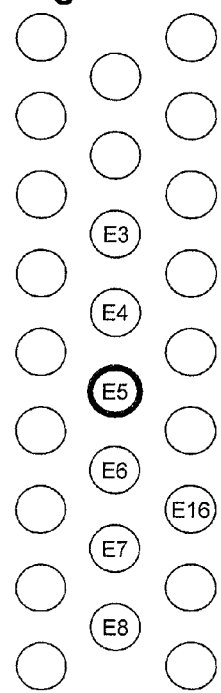

Electrode E5, which is the fifth listed reference electrode in Table 1a, is designated as the reference electrode to be currently examined, since it does have at least one neighbor electrode that has not been previously assigned to the electrode grid, in which case, the grid position that electrode E5 was previously assigned to is designated as the current reference grid position (FIG. 17c). Electrode E3, as the fourth and next unassigned neighbor electrode to electrode E5, is assigned to grid position #1 relative to the grid position to which electrode E4 is assigned, since electrode E3, while not sequential to electrode E5, is sequential to, and a lesser number than, electrode E4, a neighbor electrode previously assigned to the electrode grid relative to the current reference grid position.

Figure 17D:
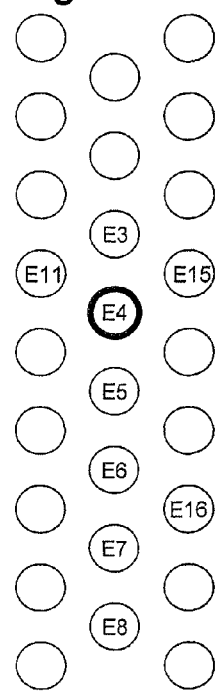

Electrode E4, which is the sixth listed reference electrode in Table 1a, is designated as the reference electrode to be currently examined, since it does have at least one neighbor electrode that has not been previously assigned to the electrode grid, in which case, the grid position that electrode E4 was previously assigned to is designated as the current reference grid position (FIG. 17d). Electrode E15, as the fourth and next unassigned neighbor electrode to electrode E4, is assigned to grid position #3 relative to the current reference grid position, since electrode E15 is not sequential to electrode E4 or any other neighbor electrode previously assigned to a position relative to the current reference grid position, but is sequential to electrode E16, an electrode previously assigned to a grid position in the same column in which grid position #3 relative to the current reference grid position is located. Electrode E11, as the fifth and next unassigned neighbor electrode to electrode E4, is assigned to grid position #5 relative to the current reference grid position, since electrode E11 is not sequential to electrode E4 or the other previously assigned neighbor electrode E15, and is not sequential to electrodes E15 and E16, two electrodes previously assigned to a grid position in the same column in which grid positions #3 and #4 relative to the current reference grid position are located.

Figure 17E:
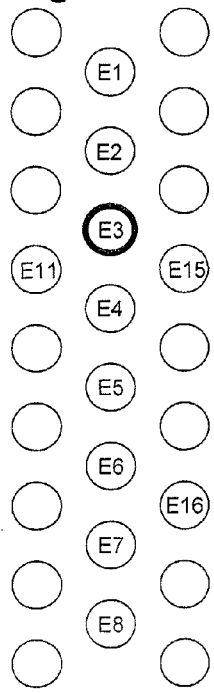

Electrode E3, which is the seventh listed reference electrode in Table 1a, is designated as the reference electrode to be currently examined, since it does have at least one neighbor electrode that has not been previously assigned to the electrode grid, in which case, the grid position that electrode E3 was previously assigned to is designated as the current reference grid position (FIG. 17e). Electrode E2, as the fifth neighbor electrode to electrode E3, is assigned to grid position #1 relative to the current reference grid position, since electrode E2 is sequential to, and has a lower number than, electrode E3. Electrode E1, as the sixth and next unassigned neighbor electrode to electrode E3, is assigned to grid position #1 relative to the grid position to which electrode E2 is assigned, since electrode E1, while not sequential to electrode E3, is sequential to, and a lesser number than, electrode E2, a neighbor electrode previously assigned to the electrode grid relative to the current reference grid position.

Electrodes E15 and E11, which are the eighth and ninth listed reference electrodes in Table 1a, do not have any neighbor electrodes that have not been previously assigned to the electrode grid, and therefore, are not designated as reference electrodes for current examination.

Figure 17F:
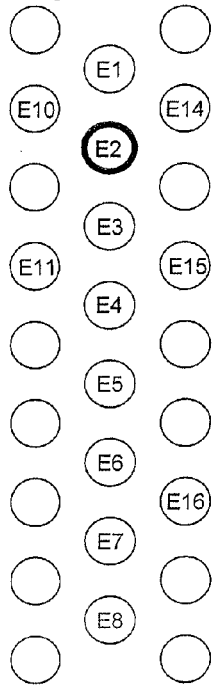

Electrode E2, which is the tenth listed reference electrode in Table 1a, is designated as the reference electrode to be currently examined, since it does have at least one neighbor electrode that has not been previously assigned to the electrode grid, in which case, the grid position that electrode E2 was previously assigned to is designated as the current reference grid position (FIG. 17f). Electrode E10, as the fourth and next unassigned neighbor electrode to electrode E2, is assigned to grid position #5 relative to the current reference grid position, since electrode E10 is not sequential to electrode E2, but is sequential to electrode E11, an electrode previously assigned to a grid position in the same column in which grid position #5 relative to the current reference grid position is located. Electrode E14, as the fifth and next unassigned neighbor electrode to electrode E2, is assigned to grid position #3 relative to the current reference grid position, since electrode E14 is not sequential to electrode E2, but is sequential to electrode E15, an electrode previously assigned to a grid position in the same column in which grid position #3 relative to the current reference grid position is located.

Figure 17G:
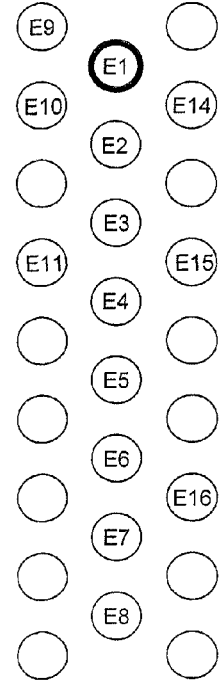

Electrode E1, which is the eleventh listed reference electrode in Table 1a, is designated as the reference electrode to be currently examined, since it does have at least one neighbor electrode that has not been previously assigned to the electrode grid, in which case, the grid position that electrode E1 was previously assigned to is designated as the current reference grid position (FIG. 17g). Electrode E9, as the fifth and next unassigned neighbor electrode to electrode E1, is assigned to grid position #5 relative to the current reference grid position, since electrode E9 is not sequential to electrode E2, but is sequential to electrode E10, an electrode previously assigned to a grid position in the same column in which grid position #5 is located.

Electrode E10, which is the twelfth listed reference electrode in Table 1a, does not have any neighbor electrodes that have not been previously assigned to the electrode grid, and therefore, is not designated as a reference electrode for current examination.

Figure 17H:
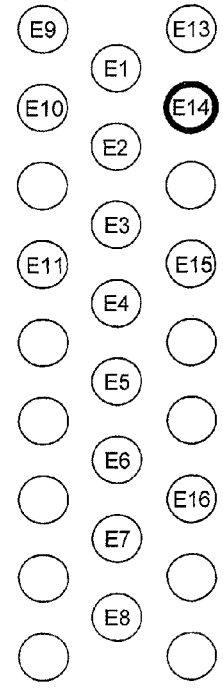

Electrode E14, which is the thirteen listed reference electrode in Table 1a, is designated as the reference electrode to be currently examined, since it does have at least one neighbor electrode that has not been previously assigned to the electrode grid, in which case, the grid position that electrode E14 was previously assigned to is designated as the current reference grid position (FIG. 17h). Electrode E13, as the third and next unassigned neighbor electrode to electrode E14, is assigned to grid position #1 relative to the current reference grid position, since electrode E13 is sequential to, and has a lower number than, electrode E14.

Electrodes E9 and E13, which are the fourteen and fifteenth listed reference electrodes in Table 1a, do not have any neighbor electrodes that have not been previously assigned to the electrode grid, and therefore, are not designated as reference electrodes for current examination. As discussed above, electrode E12 could not be used to take proximity measurements, and therefore, could not be used in the method illustrated in FIG. 14. However, because it is known that electrode E12 is sequential to, and a higher number than, electrode E11, electrode E12 can be assigned to the electrode grid somewhere below electrode E11.

Although the foregoing electrode cluster and programming techniques have been described as being implemented in the CP 18, it should be noted that these techniques are not computationally intensive, such that they may be alternatively or additionally implemented in the RC 16.

As another example, and with reference to FIG. 18*a*-18*m*, the assignment of electrodes of the configuration illustrated in FIG. 13*b* to the electrode grid will now be discussed. For clarity, the bolded circle in each iteration described with respect to FIGS. 18*a*-18*m* represents the reference electrode grid position.

Figure 18A:
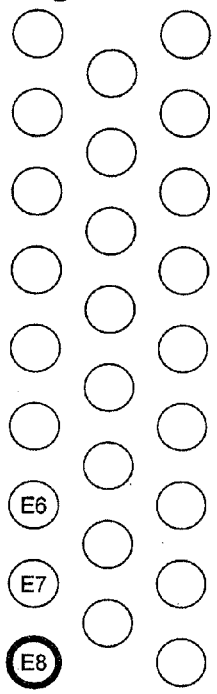
FIGS. 18a-18l are plan views illustrating the iterative assignment of electrodes from the neurostimulation lead configuration of FIG. 13b to the electrode grid of FIG. 15 by the SCS system of FIG. 1 in accordance with the technique performed in FIG. 14.

Electrode E8, which is the first listed reference electrode in Table 1b, is designated as the reference electrode to be currently examined, and is then assigned to a reference grid position (FIG. 18*a*). Electrode E7, as the first neighbor electrode to electrode E8, is assigned to grid position #1 relative to the current reference grid position, since electrode E7 is sequential to, and has a lower number than, electrode E8. Electrode E6, as the second and next unassigned neighbor electrode to electrode E8, is assigned to grid position #1 relative to the grid position to which electrode E7 is assigned, since electrode E6, while not sequential to electrode E8, is sequential to, and a lesser number than, electrode E7, a neighbor electrode previously assigned to the electrode grid relative to the current reference grid position.

Figure 18B:
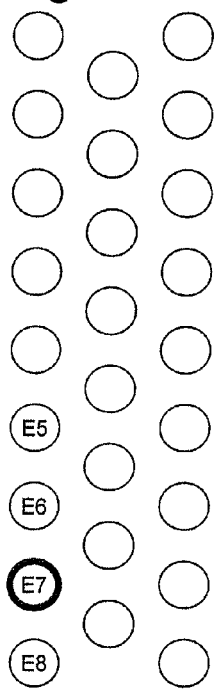

Electrode E7, which is the second listed reference electrode in Table 1b, is designated as the reference electrode to be currently examined, since it does have at least one neighbor electrode that has not been previously assigned to the electrode grid, in which case, the grid position that electrode E7 was previously assigned to is designated as the current reference grid position (FIG. 18*b*). Electrode E5, as the third and next unassigned neighbor electrode to electrode E7, is assigned to grid position #1 relative to the grid position to which electrode E6 is assigned, since electrode E5, while not sequential to electrode E7, is sequential to, and a lesser number than, electrode E6, a neighbor electrode previously assigned to the electrode grid relative to the current reference grid position.

Figure 18C:
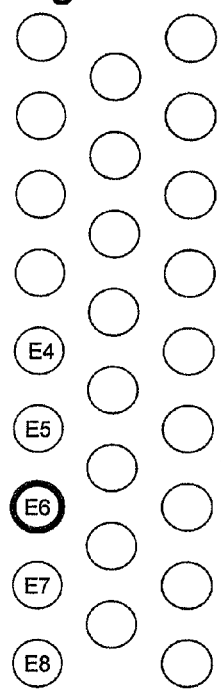

Electrode E6, which is the third listed reference electrode in Table 1b, is designated as the reference electrode to be currently examined, since it does have at least one neighbor electrode that has not been previously assigned to the electrode grid, in which case, the grid position that electrode E6 was previously assigned to is designated as the current reference grid position (FIG. 18*c*). Electrode E4, as the fourth and next unassigned neighbor electrode to electrode E6, is assigned to grid position #1 relative to the grid position to which electrode E5 is assigned, since electrode E4, while not sequential to electrode E6, is sequential to, and a lesser number than, electrode E5, a neighbor electrode previously assigned to the electrode grid relative to the current reference grid position.

Figure 18D:
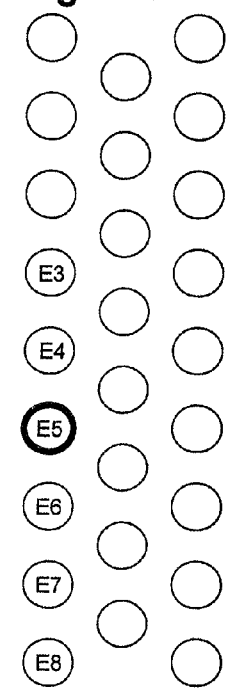

Electrode E5, which is the fourth listed reference electrode in Table 1b, is designated as the reference electrode to be currently examined, since it does have at least one neighbor electrode that has not been previously assigned to the electrode grid, in which case, the grid position that electrode E5 was previously assigned to is designated as the current reference grid position (FIG. 18*d*). Electrode E3, as the fourth and next unassigned neighbor electrode to electrode E5, is assigned to grid position #1 relative to the grid position to which electrode E4 is assigned, since electrode E3, while not sequential to electrode E5, is sequential to, and a lesser number than, electrode E4, a neighbor electrode previously assigned to the electrode grid relative to the current reference grid position.

Figure 18E:
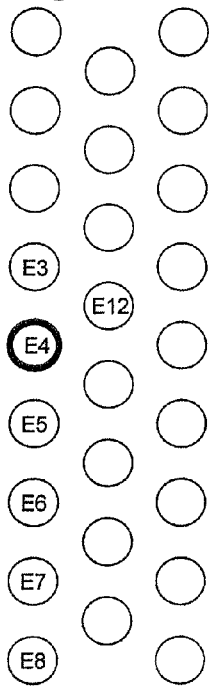

Electrode E4, which is the fifth listed reference electrode in Table 1b, is designated as the reference electrode to be currently examined, since it does have at least one neighbor electrode that has not been previously assigned to the electrode grid, in which case, the grid position that electrode E4 was previously assigned to is designated as the current reference grid position (FIG. 18*e*). Electrode E12, as the fourth neighbor electrode to electrode E4, is assigned to grid position #3 relative to the current reference grid position, since electrode E12 is not sequential to electrode E4 or electrode E3, a neighbor electrode previously assigned to the electrode grid relative to the current reference grid position, and no other electrode has been previously assigned to a grid position in the same columns in which grid positions #5 or #6 relative to the current reference grid position are located.

Figure 18F:
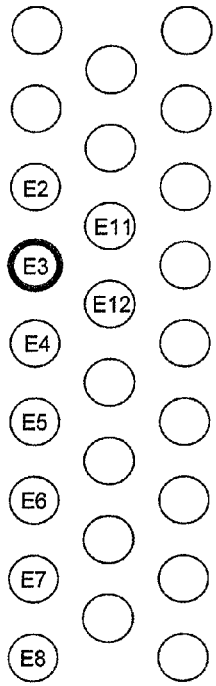

Electrode E3, which is the sixth listed reference electrode in Table 1b, is designated as the reference electrode to be currently examined, since it does have at least one neighbor electrode that has not been previously assigned to the electrode grid, in which case, the grid position that electrode E3 was previously assigned to is designated as the current reference grid position (FIG. 18*f*). Then, electrode E2, as the fourth neighbor electrode to electrode E3, is assigned to grid position #1 relative to the current reference grid position, since electrode E2 is sequential to, and has a lower number than, electrode E3. Electrode E11, as the fifth and next unassigned neighbor electrode to electrode E3, is assigned to grid position #3 relative to the current reference grid position, since electrode E11 is not sequential to electrode E3 or any other neighbor electrode previously assigned to a position relative to the current reference grid position, but is sequential to electrode E12, an electrode previously assigned to a grid position in the same column in which grid position #3 relative to the current reference grid position is located.

Figure 18G:
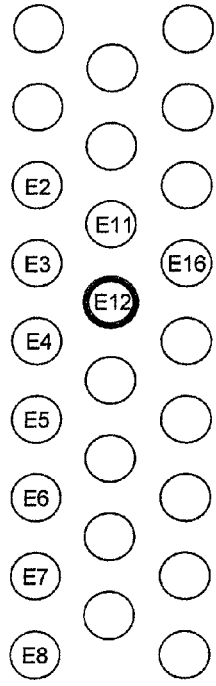

Electrode E12, which is the seventh listed reference electrode in Table 1a, is designated as the reference electrode to be currently examined, since it does have at least one neighbor electrode that has not been previously assigned to the electrode grid, in which case, the grid position that electrode E12 was previously assigned to is designated as the current reference grid position (FIG. 18*g*). Electrode E16, as the third and next unassigned neighbor electrode to electrode E12, is assigned to grid position #3 relative to the current reference grid position, since electrode E16 is not sequential to electrode E12 or any other neighbor electrode previously assigned to a position relative to the current reference grid position, and is not sequential to electrodes E2-E8, electrodes previously assigned to a grid position in the same column in which grid positions #5 and #6 relative to the current reference grid position are located.

Figure 18H:
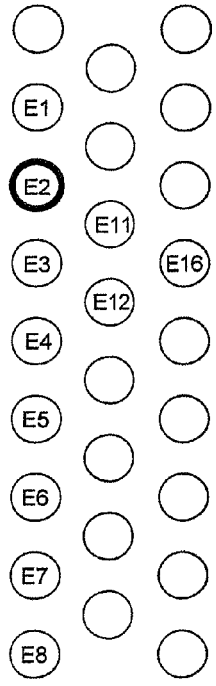

Electrode E2, which is the eighth listed reference electrode in Table 1a, is designated as the reference electrode to be currently examined, since it does have at least one neighbor electrode that has not been previously assigned to the electrode grid, in which case, the grid position that electrode E2 was previously assigned to is designated as the current reference grid position (FIG. 18*h*). Electrode E1, as the fourth neighbor electrode to electrode E2, is assigned to grid position #1 relative to the current reference grid position, since electrode E1 is sequential to, and has a lower number than, electrode E2.

Figure 18I:
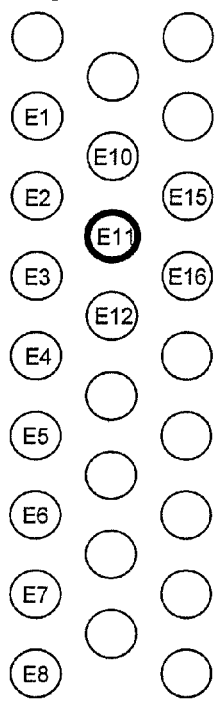

Electrode E11, which is the ninth listed reference electrode in Table 1a, is designated as the reference electrode to be currently examined, since it does have at least one neighbor electrode that has not been previously assigned to the electrode grid, in which case, the grid position that electrode E11 was previously assigned to is designated as the current reference grid position (FIG. 18*i*). Electrode E15, as the fifth and next unassigned neighbor electrode to electrode E11, is assigned to grid position #3 relative to the current reference grid position, since electrode E15 is not sequential to electrode E11 or any other neighbor electrode previously assigned to a position relative to the current reference grid position, but is sequential to electrode E16, an electrode previously assigned to a grid position in the same column in which grid position #3 relative to the current reference grid position is located. Electrode E10, as the sixth and next unassigned neighbor electrode to electrode E11, is assigned to grid position #1 relative to the current reference grid position, since electrode E10 is sequential to, and has a lower number than, electrode E11.

Electrodes E1 and E16, which are the tenth and eleventh listed reference electrodes in Table 1b, do not have any neighbor electrodes that have not been previously assigned to the electrode grid, and therefore, are not designated as reference electrodes for current examination.

Figure 18J:
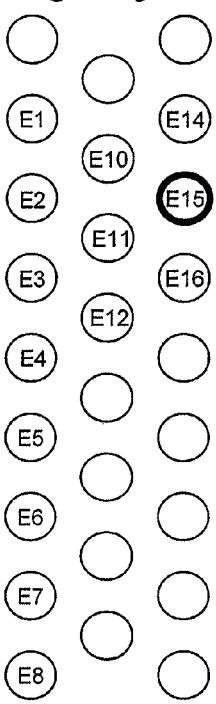

Electrode E15, which is the twelfth listed reference electrode in Table 1b, is designated as the reference electrode to be currently examined, since it does have at least one neighbor electrode that has not been previously assigned to the electrode grid, in which case, the grid position that electrode E15 was previously assigned to is designated as the current reference grid position (FIG. 18*j*). Electrode E14, as the fourth and next unassigned neighbor electrode to electrode E15, is assigned to grid position #1 relative to the current reference grid position, since electrode E14 is sequential to, and has a lower number than, electrode E15.

Figure 18K:
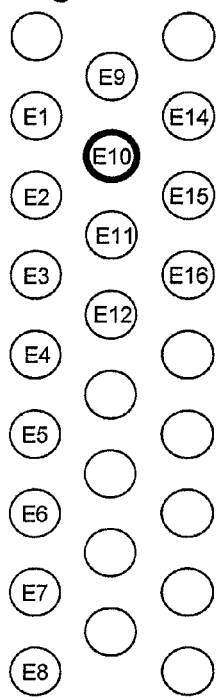

Electrode E10, which is the thirteen listed reference electrode in Table 1b, is designated as the reference electrode to be currently examined, since it does have at least one neighbor electrode that has not been previously assigned to the electrode grid, in which case, the grid position that electrode E10 was previously assigned to is designated as the current reference grid position (FIG. 18*k*). Electrode E9, as the fourth and next unassigned neighbor electrode to electrode E10, is assigned to grid position #1 relative to the current reference grid position, since electrode E9 is sequential to, and has a lower number than, electrode E10.

Figure 18L:
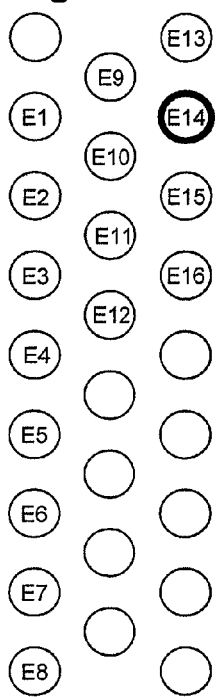

Electrode E14, which is the fourteen listed reference electrode in Table 1b, is designated as the reference electrode to be currently examined, since it does have at least one neighbor electrode that has not been previously assigned to the electrode grid, in which case, the grid position that electrode E14 was previously assigned to is designated as the current reference grid position (FIG. 18*l*). Electrode E13, as the fourth and next unassigned neighbor electrode to electrode E14, is assigned to grid position #1 relative to the current reference grid position, since electrode E13 is sequential to, and has a lower number than, electrode E14.

Electrodes E9 and E13, which are the fifteen and sixteenth listed reference electrodes in Table 1b, do not have any neighbor electrodes that have not been previously assigned to the electrode grid, and therefore, are not designated as reference electrodes for current examination.

It should be noted that the electrode configuration mapping technique described above does not take into account the difference in electrode-to-electrode spacing and lead separation, and thus, the estimated map only reflects relative positions of the electrodes, rather than faithfully replicating the actual electrode positions. Conventional pattern recognition techniques (e.g., regression, template matching, maximal likelihood, optimal fitting, etc.) can be applied to the electrode configuration map to further identify the linear electrode arrays and correct possible errors or deviations that arise in the estimate due to any limitations in the rules used to assign neighbor electrodes to the electrode grid. The pattern recognition techniques may also serve to identify the linear electrode arrays consisting of non-sequential electrodes (e.g., a 1×16 linear electrode array supported by two connector ports). Once the linear electrode arrays are identified in the electrode configuration map, this information can be input to other electrode processing techniques to determine more details concerning the lead configuration, such as, e.g., lead type, stagger, separation, and/or medial-lateral order, etc.

Notably, the electrode assignment rules can be modified to be more loose or more restrictive for particular applications. In addition, pattern recognition techniques can be applied during electrode configuration mapping to confine the configuration with certain patterns. This can also serve as a real time correction to any uncertainty that may arise in the assignment of the electrodes. Furthermore, if the assumption that the electrode configuration is arranged in linear arrays is removed, and an arbitrary electrode arrangement is instead assumed, the use of nearest neighbors in the electrode configuration mapping technique may still work. However, different neighbor electrode assignment rules may have to be used to estimate the position of each neighbor electrode relative to the reference electrode. In this case, for example, if the hexagonal electrode grid is still used to represent the neighbor electrode positions, each grid position will have the same rank (i.e., the chance that the grid position will be assigned an electrode will be equal). Instead of assigning each neighbor electrode to a grid position one-after-another, grid positions for all the neighbor electrodes need to be assigned simultaneously.

In this case, the neighbor electrode assignment rules described above will not apply. Instead, a pattern recognition technique may be implemented here to estimate the most likely electrode arrangement. By permutation and combination, a set of grid position assignments for all possible neighbor electrode arrangements can be obtained. For each set of grid position assignments, one can compute the pair-wise electrode proximities that are expected for this "assumed" electrode arrangement, and then compare the measured pair-wise electrode proximities to check for similarity. The grid position assignment that results in the computed electrode proximity pattern that best matches the measured electrode proximity pattern may be estimates as the most likely electrode arrangement.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neurostimulation control system for use with a plurality of electrodes, comprising:
　a user interface configured for receiving an input from a user;
　at least one processor configured for, in response to the input from the user, (a) initially assigning the electrodes to a plurality of electrode subsets to be evaluated, (b) determining a pair of immediately neighboring electrode subsets, (c) merging the pair of immediately neighboring electrode subsets into a new electrode subset (d) including the new electrode subset within the plurality of electrode subsets to be evaluated while excluding the pair of immediately neighboring electrode subsets that were merged from the plurality of electrode sets to be evaluated, (e) repeating steps (b)-(d), and (f) identifying a clustering relationship of the electrodes based at least in part on step (e); and a controller configured for programming the electrodes based on the identified clustering relationship of the electrodes.

2. The neurostimulation control system of claim 1, wherein the at least one processor is configured for determining the pair of immediately neighboring electrode subsets by determining relative proximities between pairs of the electrode subsets, and selecting the pair of electrode subsets that has the minimum relative proximity therebetween as the determined pair of immediately neighboring electrode subsets.

3. The neurostimulation control system of claim 2, wherein the at least one processor is configured for selecting the pair of electrode subsets as the determined pair of immediately neighboring electrode subsets by determining one of the following: (1) the minimum electrode electrode proximity the respective pair of electrode subsets; (2) the maximum electrode proximity between the respective pair of electrode subsets; and (3) the average electrode proximity between the respective pair of electrode subsets.

4. The neurostimulation control system of claim 1, further comprising monitoring circuitry configured for generating an electrical signal and measuring an electrical parameter between electrodes in response to the electrical signal, wherein the at least one processor is configured for determining the pair of immediately neighboring electrodes of the electrode subsets to be evaluated based on the measured electrical parameter.

5. The neurostimulation control system of claim 4, wherein the electrical parameter is an electrical field potential.

6. The neurostimulation control system of claim 1, wherein the at least one processor is configured for determining a pair of electrode subsets closest in proximity to each other than any other pair of electrode subsets as the pair of immediately neighboring electrode subsets.

7. The neurostimulation control system of claim 6, wherein the at least one processor is configured for identifying the clustering relationship of the electrodes comprises by arranging the electrodes in hierarchical clustering structures.

8. The neurostimulation control system of claim 1, wherein the at least one processor is configured for including the new electrode subset and a single electrode closest in proximity to the new electrode subset within the pair of immediately neighboring electrode subsets subsequently determined during step (b).

9. The neurostimulation control system of claim 8, wherein the at least one processor is configured for identifying the clustering relationship of the electrodes by arranging the single electrodes in an order in which they are included within the pair of immediately neighboring electrode subsets.

10. The neurostimulation control system of claim 1, wherein at least one processor is configured for performing step (e) until all the electrode subsets have been merged into a single electrode subset.

11. The neurostimulation control system of claim 1, wherein the controller is configured for programming the electrodes by selecting at least one of the electrodes as a cathode and selecting at least another of the electrodes as an anode based on the identified clustering relationship of the electrodes.

12. The neurostimulation control system of claim 1, wherein the controller is configured for programming the electrodes by selecting a plurality of groups of the electrodes to create a respective plurality of stimulation regions based on the identified clustering relationship of the electrodes.

13. The neurostimulation control system of claim 1, wherein the at least one processor and the controller are contained within an external control device.

14. The neurostimulation control system of claim 1, further comprising a display configured for displaying the identified clustering relationship of the electrodes.

15. A method of programming electrodes disposed adjacent tissue of a patient in response to receiving an input from a user, comprising:
(a) initially assigning the electrodes to a plurality of electrode subsets to be evaluated;
(b) determining a pair of immediately neighboring electrode subsets;
(c) merging the pair of immediately neighboring electrode subsets into a new electrode subset;
(d) including the new electrode subset within the plurality of electrode subsets to be evaluated while excluding the pair of immediately neighboring electrode subsets that were merged from the plurality of electrode sets to be evaluated;
(e) repeating steps (b)-(d);
(f) identifying a clustering relationship of the electrodes based at least in part on step (e);
(g) programming the electrodes based on the identified clustering relationship of the electrodes.

16. The method of claim 15, wherein the determining the pair of immediately neighboring electrode subsets comprises determining relative proximities between pairs of the electrode subsets, and selecting the pair of electrode subsets that has the minimum relative proximity therebetween as the determined pair of immediately neighboring electrode subsets.

17. The method of claim 16, wherein the selecting of the pair of electrode subsets as the determined pair of immediately neighboring electrode subsets comprises determining one of the following: (1) the minimum electrode proximity the respective pair of electrode subsets; (2) the maximum electrode proximity between the respective pair of electrode subsets; and (3) the average electrode proximity between the respective pair of electrode subsets.

18. The method of claim 15, wherein the determining the pair of immediately neighboring electrodes of the electrode subsets to be evaluated comprises generating an electrical signal, and measuring an electrical parameter between electrodes in response to the electrical signal.

19. The method of claim 18, wherein the electrical parameter is an electrical field potential.

20. The method of claim 15, wherein a pair of electrode subsets closest in proximity to each other than any other pair of electrode subsets is determined as the pair of immediately neighboring electrode subsets.

21. The method of claim 20, wherein the identifying of the clustering relationship of the electrodes comprises arranging the electrodes in hierarchical clustering structures.

22. The method of claim 15, wherein the new electrode subset and a single electrode closest in proximity to the new electrode subset are included within the pair of immediately neighboring electrode subsets subsequently determined during step (b).

23. The method of claim 22, wherein the identifying of the clustering relationship of the electrodes comprises arranging the single electrodes in an order in they are included within the pair of immediately neighboring electrode subsets.

24. The method of claim 15, wherein step (e) is performed until all the electrode subsets have been merged into a single electrode subset.

25. The method of claim 15, wherein programming the electrodes comprises selecting at least one of the electrodes as a cathode and selecting at least another of the electrodes as an anode based on the identified clustering relationship of the electrodes.

26. The method of claim 15, wherein programming the electrodes comprises selecting a plurality of groups of the electrodes to create a respective plurality of stimulation regions based on the identified clustering relationship of the electrodes.

* * * * *